(12) United States Patent
Shoaib et al.

(10) Patent No.: US 8,780,786 B2
(45) Date of Patent: Jul. 15, 2014

(54) METHOD AND APPARATUS FOR DENOISING OF PHYSIOLOGICAL SIGNALS

(75) Inventors: Mohammed Shoaib, Princeton, NJ (US); Gene Wesley Marsh, Encinitas, CA (US); Harinath Garudadri, San Diego, CA (US); Somdeb Majumdar, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 100 days.

(21) Appl. No.: 13/484,105

(22) Filed: May 30, 2012

(65) Prior Publication Data

US 2013/0070792 A1 Mar. 21, 2013

Related U.S. Application Data

(60) Provisional application No. 61/535,298, filed on Sep. 15, 2011.

(51) Int. Cl.
*H04B 7/185* (2006.01)
(52) U.S. Cl.
USPC .......................................... 370/317; 370/542
(58) Field of Classification Search
USPC ................................................. 370/542, 317
See application file for complete search history.

(56) References Cited

U.S. PATENT DOCUMENTS

| | | |
|---|---|---|
| 6,424,960 B1 | 7/2002 | Lee et al. |
| 7,565,194 B2 | 7/2009 | Tan et al. |
| 7,672,717 B1 | 3/2010 | Zikov et al. |
| 7,941,205 B2 | 5/2011 | Jung et al. |
| 2011/0015532 A1 | 1/2011 | Koertge et al. |
| 2012/0071730 A1* | 3/2012 | Romero ......................... 600/301 |
| 2012/0232417 A1* | 9/2012 | Zhang ............................ 600/518 |

FOREIGN PATENT DOCUMENTS

EP 2430975 A1 3/2012

OTHER PUBLICATIONS

Acharyya, et al., "Robust Channel Identification Scheme: Solving Permutation Indeterminacy of ICA for Artifacts Removal from ECG", 32nd Annual International Conference of the IEEE EMBS Buenos Aires, Argentina, Aug. 31-Sep. 4, 2010, 4pgs.
Actel, "IGLOO nano Low-Power Flash FPGA", Actel Inc., Aug. 2010, 132pgs.
ANSI/AAMI, "EC57: Testing and reporting performance results of cardiac rhythm and ST-segment", ANSI/AAMI EC57:1998, AAMI, 1998, 8pgs.
ECRI, "American heart association (AHA) ECG database", ECRI Institute, http://www.ecri.org/, 2012, 1 pg.
Estrin, et al., "Connecting the physical world with pervasive networks", IEEE Pervasive Computing, Mar. 2002, pp. 59-69.

(Continued)

*Primary Examiner* — Sai-Ming Chan
(74) *Attorney, Agent, or Firm* — Paul S. Holdaway

(57) ABSTRACT

Certain aspects of the present disclosure relate to techniques for denoising of physiological signals. A signal (e.g., physiological signal) comprising at least two signal channels can be decomposed (e.g., using independent component analysis (ICA)) into at least two independent components. Then, independent component (IC) denoising can be applied to estimate which of the at least two independent components belong to a signal space and which of the at least two independent components belong to a noise space using a statistical metric associated with the at least two signal channels. A de-noised version of the signal can be generated by preserving in the signal only one or more independent components of the at least two independent components belonging to the signal space.

38 Claims, 22 Drawing Sheets

(56) References Cited

OTHER PUBLICATIONS

Friesen, et al., "A comparison of the noise sensitivity of nine QRS detection algorithms," IEEE Trans. Biomed. Engineering, vol. 37, No. 1, 1990, pp. 85-98.

Hamilton, et al., "Comparison of methods for adaptive removal of motion artifact," Computers in Cardiology, IEEEE, 2000, pp. 383-386.

He, et al., "Application of independent component analysis in removing artefacts (ICA) from the electrocardiogram (ECG)", Neural Computing & App., vol. 15, 2006, 12pgs.

Himberg, et al., "Validating the independent components of neuroimaging time series via clustering and visualization", Neurolmage, vol. 22, No. 3, 2004, pp. 1214-1222.

Hyvarinen, et al., "A fast fixed-point algorithm for independent component analysis", Neural Computation, vol. 9, 1997, pp. 1483-1492.

Hyvarinen, et al., "Independent component analysis: Algorithms & applications" J. Neural Networks, vol. 13, No. 4-5, Jun. 2000, pp. 411-430.

James, et al., "Independent component analysis for biomedical signals," Physiological Meas., vol. 26, 2005, pp. 15-39.

Milanesi, et al., "Independent component analysis applied to the removal of motion artifacts from the electrocardiographic signals," Med. and Bio Engineering and Computing, vol. 46, No. 3, 2008, pp. 251-261.

Mortara, "Veritas arrhythmia and ST segmentation analysis software", Mortara Instrument, 2012, 1pg.

Nonin, "Fingertip Pulse Oximeter", Nonin Medical Inc., 2012, 2pgs.

Pan, et al., "A real time QRS detection algorithm", IEEE Trans. Biomedical Engineering, 1 vol. BME-32, No. 3, 1985, pp. 232-236.

Physionet, "MIT-BIH Noise Stress Test database", Physionet, 2000, 3pgs.

Physionet, "PTB diagnostic ECG database", http://www.physionet.org/physiobank/database, 2000, 2 pgs.

Pottie, et al., "Wireless integrated network sensors", ACM Communications, vol. 43, No. 5, 2000, pp. 51-58.

Sameni, et al., "What ICA Provides for ECG Processing: Application to Noninvasive Fetal ECG Extraction", IEEE Int. Symp. Signal Proc. And Info. Tech., Aug. 2006, pp. 656-661.

Texas Instruments, "Low-Power, 8-Channel, 16-Bit Analog Front-End for Biopotential Measurements", Texas Instruments Inc., 2011, 76pgs.

Thakor, et al., "Applications of adaptive filtering to ECG analysis: Noise cancellation and arrhythmia detection", IEEE Tran. Biomed. Engineering, vol. 38, No. 8, Aug. 1991, pp. 785-794.

Chawla M. P. S., "A comparative analysis of principal component and independent component techniques for electrocardiograms", Neural Computing and Applications, Jul. 23, 2008, pp. 539-556, vol. 18, No. 6, Springer-Verlag, LO, XP019741424, ISSN: 1433-3058.

International Search Report and Written Opinion—PCT/US2012/055493—ISA/EPO—Jan. 17, 2013.

Llinares, R. et al., "Independent Component Analysis of Body Surface Potential Mapping Recordings with Atrial Fibrillation", International Joint Conference on Neural Network (IJCNN), Jul. 16, 2006, pp. 2287-2294, IEEE Operations Center, Piscataway, NJ, USA, XP010948480, DOI: 10.1109/IJCNN.2006.1716397, ISBN: 978-0-7803-9490-2.

Martis R. J. et al., "A two-stage mechanism for registration and classification of ECG using Gaussian mixture model", Pattern Recognition, Nov. 1, 2009, vol. 42, No. 11, Elsevier, GB, pp. 2979-2988, XP026250884, ISSN: 0031-3203, DOI: 10. 1016/J.PATCOG.2009.02.008 [retrieved on Mar. 5, 2009].

Owis, M. I. et al., "Characterisation of Electrocardiogram Signals Based on Blind Source Separation", Medical and Biological Engineering and Computing, Sep. 1, 2002, pp. 557-564, vol. 40, No. 5, Springer, Heildelberg, DE, XP001186048, ISSN: 0140-0118, DOI: 10.1007/BF02345455.

Shoaib, Mohammed et al., "A closed-loop system for artifact mitigation in ambulatory electrocardiogram monitoring", Design, Automation & Test in Europe Conference & Exhibition (Date), Mar. 12, 2012, pp. 431-436, IEEE, XP032153978, ISBN: 978-1-4577-2145-8.

\* cited by examiner

| | Kurtosis | VarMean | | VarMed | | VarVar | |
|---|---|---|---|---|---|---|---|
| | VALUE | VALUE | INDEX | VALUE | INDEX | VALUE | INDEX |
| IC#1 (noise) | 0.0505 | 0.8248 | 0.0018 | 0.9323 | 0.0002 | 0.1734 | 0.0849 |
| IC#2 (ECG) | 0.0344 | 0.1111 | 0.0093 | 0.0592 | 0.0027 | 0.2131 | 0.0470 |
| IC#3 (ECG) | 0.3982 | 0.0419 | 0.2856 | 0.0043 | 0.4317 | 0.2713 | 0.4277 |
| IC#4 (ECG) | 0.5169 | 0.0221 | 0.7032 | 0.0043 | 0.5653 | 0.3421 | 0.4403 |
| SINR of frame | | 13.54 dB | | 13.54 dB | | 11.05 dB | |

Evaluation on AHA Database

| SNR | Q Se (%) | Q +P (%) | V Se (%) | V +P (%) | V FPR | # QRS | # VEB |
|---|---|---|---|---|---|---|---|
| Baseline<br>TTQA | 99.78<br>99.78 | 99.87<br>99.87 | 93.43<br>93.43 | 98.25<br>98.51 | 0.169<br>0.150 | 354324<br>354324 | 32544<br>32620 |
| -9 dB<br>TTQA | 90.56<br>99.69 | 90.64<br>99.78 | 84.79<br>93.34 | 89.41<br>98.42 | 0.266<br>0.160 | 321561<br>353981 | 29609<br>32597 |
| -3 dB<br>TTQA | 92.02<br>99.71 | 92.08<br>99.81 | 86.17<br>93.38 | 90.84<br>98.45 | 0.234<br>0.150 | 326742<br>354018 | 30082<br>32598 |
| 0 dB<br>TTQA | 93.29<br>99.72 | 93.35<br>99.83 | 87.35<br>93.39 | 92.09<br>98.45 | 0.216<br>0.150 | 331273<br>354109 | 30496<br>32602 |
| +3 dB<br>TTQA | 94.31<br>99.72 | 94.38<br>99.82 | 88.32<br>93.39 | 93.10<br>98.45 | 0.210<br>0.150 | 334905<br>354046 | 30830<br>32600 |
| +9 dB<br>TTQA | 99.65<br>99.75 | 99.73<br>99.86 | 93.32<br>93.42 | 98.18<br>98.29 | 0.174<br>0.150 | 353952<br>354289 | 32581<br>32613 |

FIG. 12

|  | Subject #1 | Subject #2 | Subject #3 | Subject #4 |
| --- | --- | --- | --- | --- |
| $\Delta IHR_{Noi}^{RMS}$ | 31.3 bpm | 30.9 bpm | 31.4 bpm | 33.1 bpm |
| $\Delta IHR_{Den}^{RMS}$ | 5.0 bpm | 6.4 bpm | 3.6 bpm | 3.9 bpm |

FIG. 15

METHOD AND APPARATUS FOR DENOISING OF PHYSIOLOGICAL SIGNALS

CLAIM OF PRIORITY UNDER 35 U.S.C. §119

The present Application for Patent claims benefit of U.S. Provisional Patent Application Ser. No. 61/535,298, entitled, "Method and apparatus for denoising of physiological signals", filed Sep. 15, 2011 and assigned to the assignee hereof and hereby expressly incorporated by reference herein.

BACKGROUND

1. Field

Certain aspects of the present disclosure generally relate to signal processing and, more particularly, to a method and apparatus for denoising of sensed physiological signals.

2. Background

Recent advances in mobile computing and energy-efficient communication have shown promise in the continuous acquisition, storage, and processing of physiological signals. Pervasive sensors deployed in next generation networks have enabled algorithms capable of efficient and accurate information processing. However, sensors that monitor dynamic physical systems present large volumes of noisy data with a wide range of signal artifacts. For example, in ambulatory electrocardiogram (ECG) signal monitoring, artifacts can result from the movement of electrodes on the surface of the skin, power line interference, muscle noise, and baseline-wander. Direct processing of these noisy signals suffers from poor performance of algorithms such as those used for beat detection and arrhythmia classification. Efficient techniques for the selective removal of artifact sources while retaining useful signal components are thus desirable to ensure accurate performance of algorithms which rely on ambulatory ECG data.

In the past, analog and digital filtering techniques have demonstrated great success in mitigating several noise sources in the ECG. However, motion artifacts and muscle noise present a unique challenge to these signal processing methods. Linear and non-linear denoising filters fail to effectively remove interference from electrode motion and muscle noise since these represent sources which are within the same frequency range as the cardiac signal. Traditional filtering techniques applied to the noisy recordings may thus eliminate useful ECG components corrupting the signal morphology and spectral content.

SUMMARY

Certain aspects of the present disclosure provide an apparatus for signal processing. The apparatus generally includes a circuit configured to obtain a signal that comprises at least two signal channels, an independent component analysis (ICA) module configured to decompose the signal into at least two independent components, and an independent component (IC) denoising module configured to estimate which of the at least two independent components belong to a signal space and which of the at least two independent component belong to a noise space using a statistical metric associated with the at least two signal channels, wherein the IC denoising module is also configured to generate a de-noised version of the signal by preserving in the signal only one or more independent components of the at least two independent components belonging to the signal space.

Certain aspects of the present disclosure provide a method for signal processing. The method generally includes obtaining a signal that comprises at least two signal channels, decomposing the signal into at least two independent components, estimating which of the at least two independent components belong to a signal space and which of the at least two independent components belong to a noise space using a statistical metric associated with the at least two signal channels, and generating a de-noised version of the signal by preserving in the signal only one or more independent components of the at least two independent components belonging to the signal space.

Certain aspects of the present disclosure provide an apparatus for signal processing. The apparatus generally includes means for obtaining a signal that comprises at least two signal channels, means for decomposing the signal into at least two independent components, means for estimating which of the at least two independent components belong to a signal space and which of the at least two independent components belong to a noise space using a statistical metric associated with the at least two signal channels, and means for generating a de-noised version of the signal by preserving in the signal only one or more independent components of the at least two independent components belonging to the signal space.

Certain aspects of the present disclosure provide a computer program product for signal processing. The computer program product generally includes a computer-readable medium comprising instructions executable to obtain a signal that comprises at least two signal channels, decompose the signal into at least two independent components, estimate which of the at least two independent components belong to a signal space and which of the at least two independent components belong to a noise space using a statistical metric associated with the at least two signal channels, and generate a de-noised version of the signal by preserving in the signal only one or more independent components of the at least two independent components belonging to the signal space.

BRIEF DESCRIPTION OF THE DRAWINGS

So that the manner in which the above-recited features of the present disclosure can be understood in detail, a more particular description, briefly summarized above, may be had by reference to aspects, some of which are illustrated in the appended drawings. It is to be noted, however, that the appended drawings illustrate only certain typical aspects of this disclosure and are therefore not to be considered limiting of its scope, for the description may admit to other equally effective aspects.

FIG. 12 illustrates an example of arrhythmia classification and beat detection with strong resilience to a noise after TTQA based denoising in accordance with certain aspects of the present disclosure.

FIG. 15 illustrates an example error in the estimated IHR after TTQA based denoising in accordance with certain aspects of the present disclosure.

DETAILED DESCRIPTION

Figure 1:
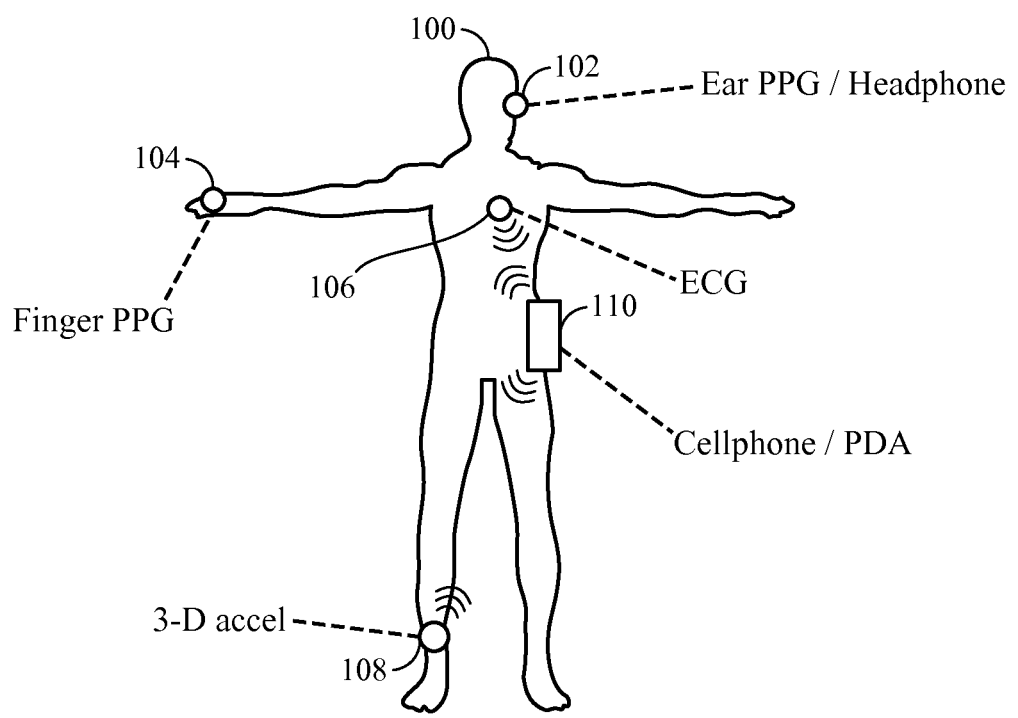
FIG. 1 illustrates an example of a body area network (BAN) in accordance with certain aspects of the present disclosure.

Various aspects of the disclosure are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim.

The word "exemplary" is used herein to mean "serving as an example, instance, or illustration." Any aspect described herein as "exemplary" is not necessarily to be construed as preferred or advantageous over other aspects.

Although particular aspects are described herein, many variations and permutations of these aspects fall within the scope of the disclosure. Although some benefits and advantages of the preferred aspects are mentioned, the scope of the disclosure is not intended to be limited to particular benefits, uses, or objectives. Rather, aspects of the disclosure are intended to be broadly applicable to different wireless technologies, system configurations, networks, and transmission protocols, some of which are illustrated by way of example in the figures and in the following description of the preferred aspects. The detailed description and drawings are merely illustrative of the disclosure rather than limiting, the scope of the disclosure being defined by the appended claims and equivalents thereof.

An Example Wireless Communication System

The techniques described herein may be used for various broadband wireless communication systems, including communication systems that are based on an orthogonal multiplexing scheme and a single carrier transmission. Examples of such communication systems include Orthogonal Frequency Division Multiple Access (OFDMA) systems, Single-Carrier Frequency Division Multiple Access (SC-FDMA) systems, Code Division Multiple Access (CDMA), and so forth. An OFDMA system utilizes orthogonal frequency division multiplexing (OFDM), which is a modulation technique that partitions the overall system bandwidth into multiple orthogonal sub-carriers. These sub-carriers may also be called tones, bins, etc. With OFDM, each sub-carrier may be independently modulated with data. An SC-FDMA system may utilize interleaved FDMA (IFDMA) to transmit on sub-carriers that are distributed across the system bandwidth, localized FDMA (LFDMA) to transmit on a block of adjacent sub-carriers, or enhanced FDMA (EFDMA) to transmit on multiple blocks of adjacent sub-carriers. In general, modulation symbols are created in the frequency domain with OFDM and in the time domain with SC-FDMA. A CDMA system may utilize spread-spectrum technology and a coding scheme where each transmitter (i.e., user) is assigned a code in order to allow multiple users to be multiplexed over the same physical channel.

The teachings herein may be incorporated into (e.g., implemented within or performed by) a variety of wired or wireless apparatuses (e.g., nodes). In some aspects, a node comprises a wireless node. Such wireless node may provide, for example, connectivity for or to a network (e.g., a wide area network such as the Internet or a cellular network) via a wired or wireless communication link. In some aspects, a wireless node implemented in accordance with the teachings herein may comprise an access point or an access terminal.

Certain aspects of the present disclosure may support methods implemented in body area networks (BANs). BANs are a promising concept for healthcare applications such as continuous monitoring for diagnostic purposes, effects of medicines on chronic ailments, and the like. FIG. 1 illustrates an example of a BAN 100 that may comprise several acquisition circuits 102, 104, 106, 108. Each acquisition circuit may comprise a wireless sensor that senses one or more vital biophysical signals and communicates them (e.g., over a wireless channel) to an aggregator (a receiver) 110 for processing purposes.

The BAN 100 may be therefore viewed as a wireless communication system where various wireless nodes (i.e., acquisition circuits and aggregator) communicate using an orthogonal multiplexing scheme, a single carrier transmission, or other suitable wireless communication technique. The aggregator 110 may be a mobile handset, a wireless watch, a headset, a monitoring device, a Personal Data Assistant (PDA), or other device configured for wireless communication. As illustrated in FIG. 1, an acquisition circuit 102 may correspond to an ear photoplethysmograph (PPG) sensor, an acquisition circuit 104 may correspond to a finger PPG sensor, an acquisition circuit 106 may correspond to an electrocardiogram (ECG) sensor (or an electroencephalogram (EEG) sensor), and an acquisition circuit 108 may correspond to a 3D-Accelerometer (3D-Accl) sensor. In an aspect, the acquisition circuits in FIG. 1 may operate in accordance with compressed sensing (CS), where an acquisition rate may be smaller than a Nyquist rate of a signal being acquired. For example, the acquisition circuits illustrated in FIG. 1 may use CS when sensing body signals.

Figure 2:
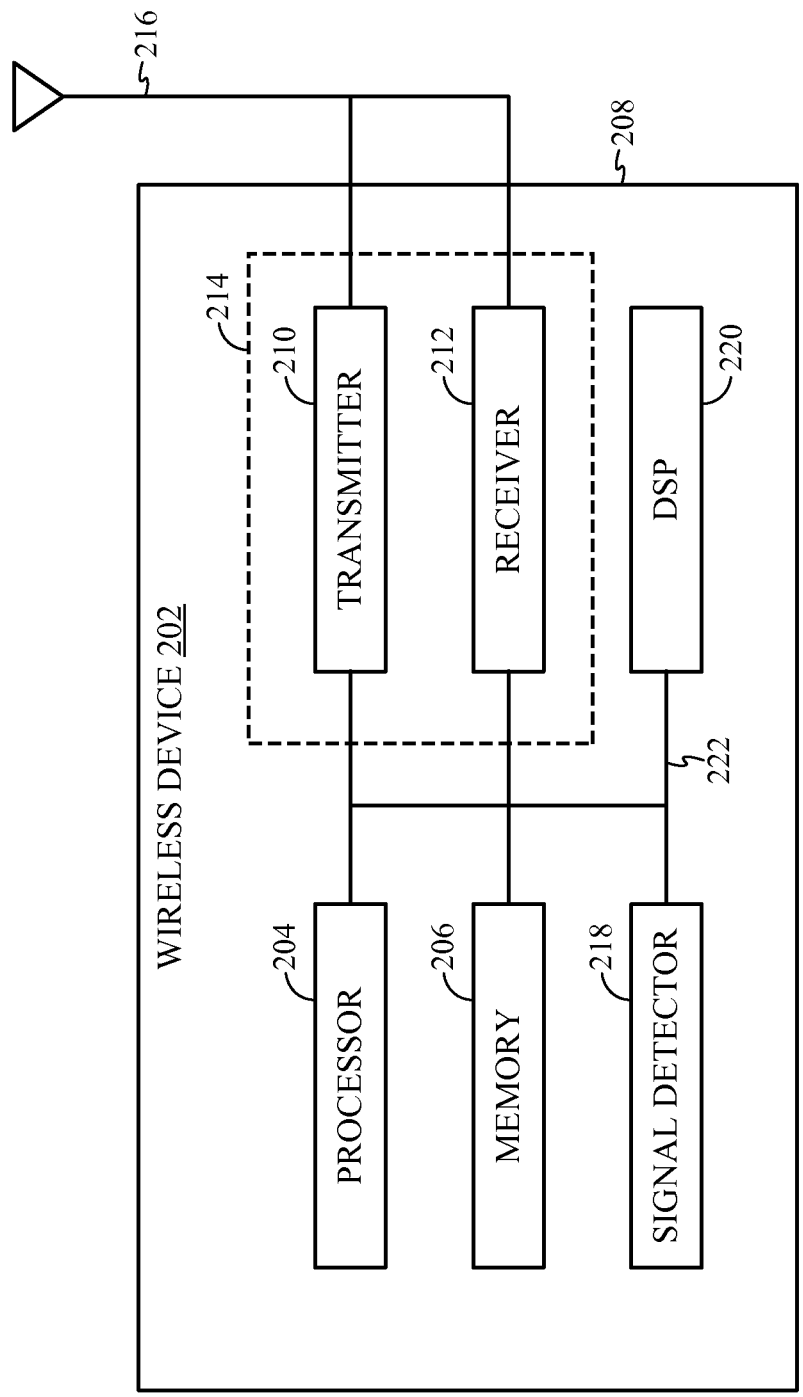
FIG. 2 illustrates various components that may be utilized in a wireless device of the BAN in accordance with certain aspects of the present disclosure.

FIG. 2 illustrates various components that may be utilized in a wireless device 202 that may be employed within the BAN 100. The wireless device 202 is an example of a device that may be configured to implement the various methods described herein. The wireless device 202 may correspond to the aggregator 110 or to one of the acquisition circuits 102, 104, 106, 108.

The wireless device 202 may include a processor 204 which controls operation of the wireless device 202. The processor 204 may also be referred to as a central processing unit (CPU). Memory 206, which may include both read-only memory (ROM) and random access memory (RAM), provides instructions and data to the processor 204. A portion of the memory 206 may also include non-volatile random access memory (NVRAM). The processor 204 typically performs logical and arithmetic operations based on program instructions stored within the memory 206. The instructions in the memory 206 may be executable to implement the methods described herein.

The processor 204 may comprise or be a component of a processing system implemented with one or more processors. The one or more processors may be implemented with any combination of general-purpose microprocessors, microcontrollers, digital signal processors (DSPs), field programmable gate array (FPGAs), programmable logic devices (PLDs), controllers, state machines, gated logic, discrete hardware components, dedicated hardware finite state machines, or any other suitable entities that can perform calculations or other manipulations of information.

The processing system may also include machine-readable media for storing software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the one or more processors, cause the processing system to perform the various functions described herein.

The wireless device 202 may also include a housing 208 that may include a transmitter 210 and a receiver 212 to allow transmission and reception of data between the wireless device 202 and another wireless node (e.g., another wireless node in a remote location). The transmitter 210 and receiver 212 may be combined into a transceiver 214. Wireless device 202 may also include one or more antennas 216 electrically coupled to the transceiver 214. The wireless device 202 may also include (not shown) multiple transmitters, multiple receivers, multiple transceivers, and/or multiple antennas.

The wireless device 202 may also include a signal detector 218 that may detect and quantify the level of signals received by the transceiver 214. The signal detector 218 may quantify detection of such signals using total energy, energy per subcarrier per symbol, power spectral density and/or other quantification metrics. The wireless device 202 may also include a digital signal processor (DSP) 220 for use in processing signals.

The various components of the wireless device 202 may be coupled by a bus system 222, which may include a power bus, a control signal bus, and a status signal bus in addition to a data bus.

Body worn sensors (e.g., the sensors 102, 104, 106, 108 of the BAN 100 from FIG. 1) are susceptible to different artifacts. Therefore, it may be desirable to denoise them reliably. Having a quality metric that describes the quality of a denoised signal is useful; however, this may not be directly measurable due to unavailability of a clean source signal. A method is described in the present disclosure for denoising physiological signals that have additional noise sources. A noisy signal may be first decomposed into independent components, and then signal and noise components may be identified and separated. A method is also described in the present disclosure to estimate the quality of the denoised signal. In addition, a method is described to ensure that output denoised signal channels may maintain the indexing of input signal channels. Finally, a closed loop system is described that utilizes the quality estimate to refine denoising parameters.

Independent Component Analysis

Independent component analysis (ICA) is a method of blind source separation which relies on the property of linear superposition of statistically independent signals to separate a signal into independent components. Its applicability to biomedical signals has recently gained interest. However, most ICA based ECG artifact mitigation algorithms rely on a visual inspection of independent components to identify sources of noise (i.e., to determine which of the independent components are noise). Although some recent methods try to automate the identification process, they are limited in their ability to function across a range of ECG morphologies present in standard databases. In the present disclosure, a robust statistical metric is provided to enable an automatic identification of the noise sources. Further, a signal-dependent metric for an automatic quality assessment of the de-noised ECG is presented, which may enable a closed-loop feedback. This approach can be demonstrated using noisy ECG signals from extensive databases as well as from active subjects in a laboratory.

Figure 3:
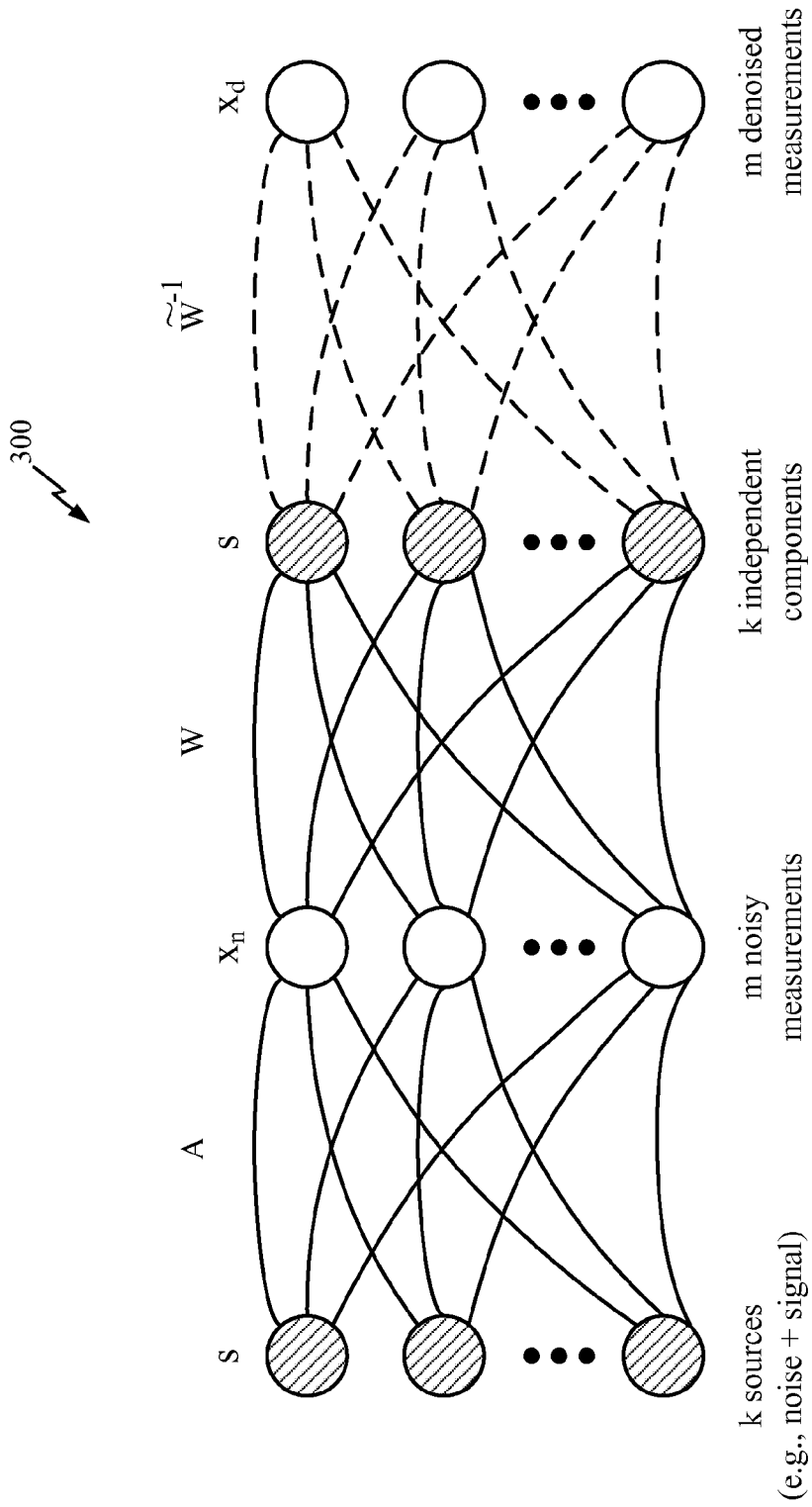
FIG. 3 illustrates an example of an independent component analysis (ICA) algorithm in accordance with certain aspects of the present disclosure.

An overview of the ICA algorithm and its application to denoise multi-lead ECG signals is first provided in the present disclosure. FIG. 3 illustrates an example 300 of the ICA algorithm in accordance with certain aspects of the present disclosure, Given a set of k independent time domain sources $s=\{s_1(t), \ldots, s_k(t)\}$ linearly mixed to produce m noisy measurements $x_n=\{x_{n,1}(t), \ldots, x_{n,m}(t)\}$ according to the relationship $$x_n = As, \quad (1)$$

where A is a mixing matrix. The ICA algorithm may provide an estimate of a de-mixing matrix W. The set of source signals (also called independent components (ICs)) can thus be recovered as s=Wx$_n$. One or more ICs of the source signals s may be associated with desired (biomedical) signals and belong to a signal space, while at least one of the ICs may be associated with a noise source and belongs to a noise space. In general, the matrices A and W may be non-stationary, non-square matrices, and ideally AW=I. According to certain aspects of the present disclosure, the noisy measurements x$_n$ from FIG. 3 may correspond to measurements of one or more physiological signals (e.g., ECG, PPG, EEG, 3D-Accl signals) obtained by one or more of the acquisition circuits (sensor devices) 102, 104, 106, 108 of the BAN 100 from FIG. 1.

In an exemplary ECG measurement system, along with electrical activity of a heart observed at an epicardium (an outer tissue of the heart), a statistically independent motion artifact and a muscle noise may be sources in the source signal set s, and may belong to the noise space. In an aspect, a linear mixture of the sources may be observed as a surface ECG signal (noisy measurements x$_n$), which may be obtained by the acquisition circuit 106 from FIG. 1. The ICA algorithm utilizes the noisy measurements x$_n$ to estimate independent signal sources s (i.e., the set of ICs) and the de-mixing matrix W. In the denoising process, a modified mixing matrix $\tilde{W}^{-1}$ may be obtained by zeroing out one or more columns of $W^{-1}$ that correspond to noise sources (noise space) in the estimated set of ICs. Thus, the denoised ECG measurements x$_d$ that belong only to the signal space can be represented as:

$$x_d = \tilde{W}^{-1} \cdot s. \quad (2)$$

As is evident from the above process, there could be two practical challenges in denoising ECG signals using the ICA. First, it may be non-trivial to automatically identify components of the signals that correspond to the noise sources (noise space) in the independent signal sources s. Second, after zeroing out columns of $W^{-1}$ that correspond to the identified noise components in s, a metric for evaluating a quality of the denoised ECG measurements may be desirable to ensure consistent quality of the denoised ECG measurements.

The first challenge above may stem from a varied range of artifacts which can appear in the ECG. For example, an electrode motion noise may appear as irregular disturbances, whereas a muscle noise can manifest itself as a wide-band Gaussian interference. The second difficulty may arise since the electrical activity of the heart at the epicardium is not directly measurable. Thus, without access to the expected denoised signal component, traditional metrics such as signal-to-noise (SNR) or signal-to-interference-plus-noise ratio (SINR) might not be usable. A technique described in the present disclosure may overcome the above challenges enhancing the practical feasibility of ICA in denoising ECG data and other physiological signals.

Certain aspects of the present disclosure support utilizing a temporally tuned quality assessment (TTQA) algorithm along with the ICA for denoising ECG data. This technique can be, for example, validated based on the Physikalisch-Technische Bundesanstalt (PTB) diagnostic ECG database. Two case studies are also presented as examples of TTQA applications: arrhythmia detection followed by instantaneous heart rate (IHR) estimation.

Temporally Tuned Quality Assessment

Figure 4:
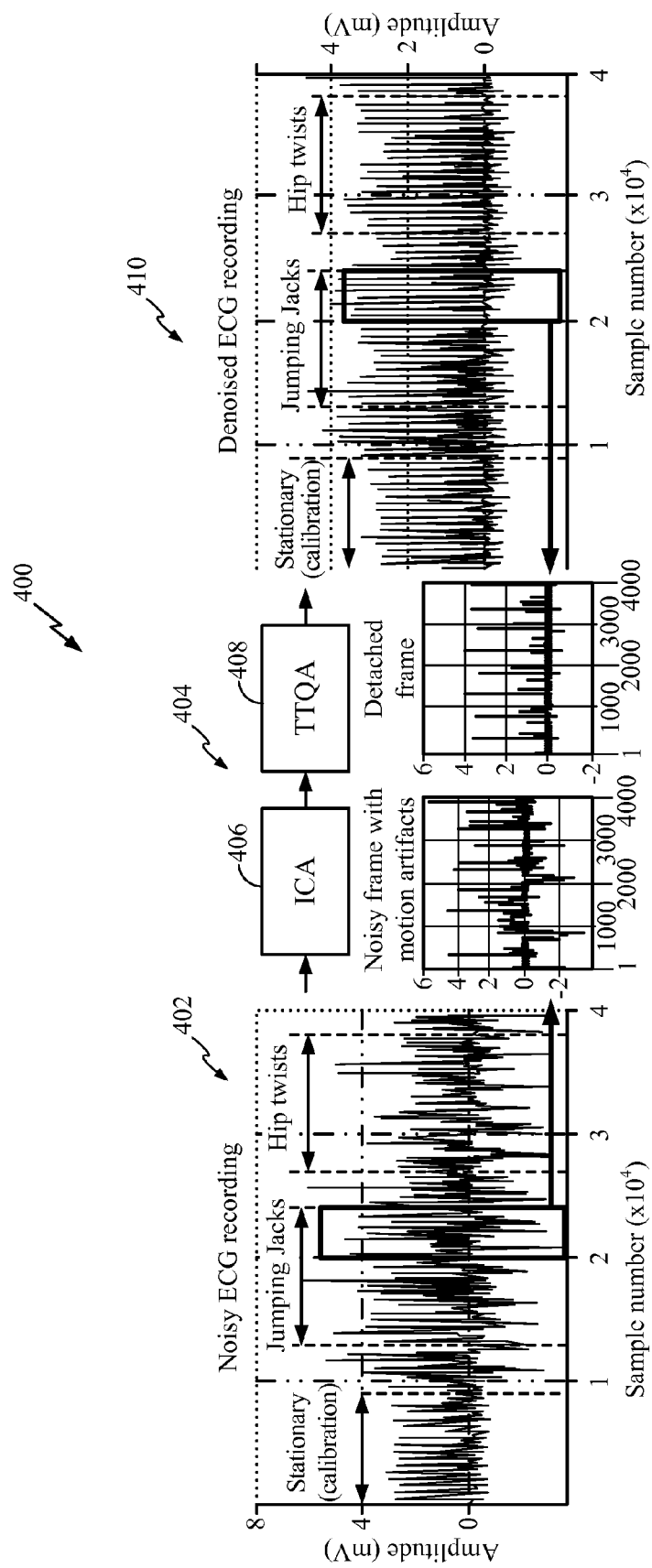
FIG. 4 illustrates an example of automatic selection of noise components and a closed-loop assessment of artifact mitigation using ICA in accordance with certain aspects of the present disclosure.

FIG. 4 illustrates example functionality 400 of the TTQA algorithm in the ICA based denoising of ECG data in accordance with certain aspects of the present disclosure. A graph 402 of FIG. 4 shows an ECG recording of a subject that performs 60 seconds each of jumping jacks and hip twists after being stationary for 60 seconds. As illustrated in a portion 404 of FIG. 4, the ICA may be performed by a unit 406 to separate statistically independent components in the noisy ECG data. After the separation process, the TTQA may be performed by a unit 408 for automatic identification of the noise components, which can be eliminated while simultaneously evaluating its effect on the quality of denoised ECG data. The denoised ECG recording thus obtained is shown in a graph 410 of FIG. 4.

Figure 5:
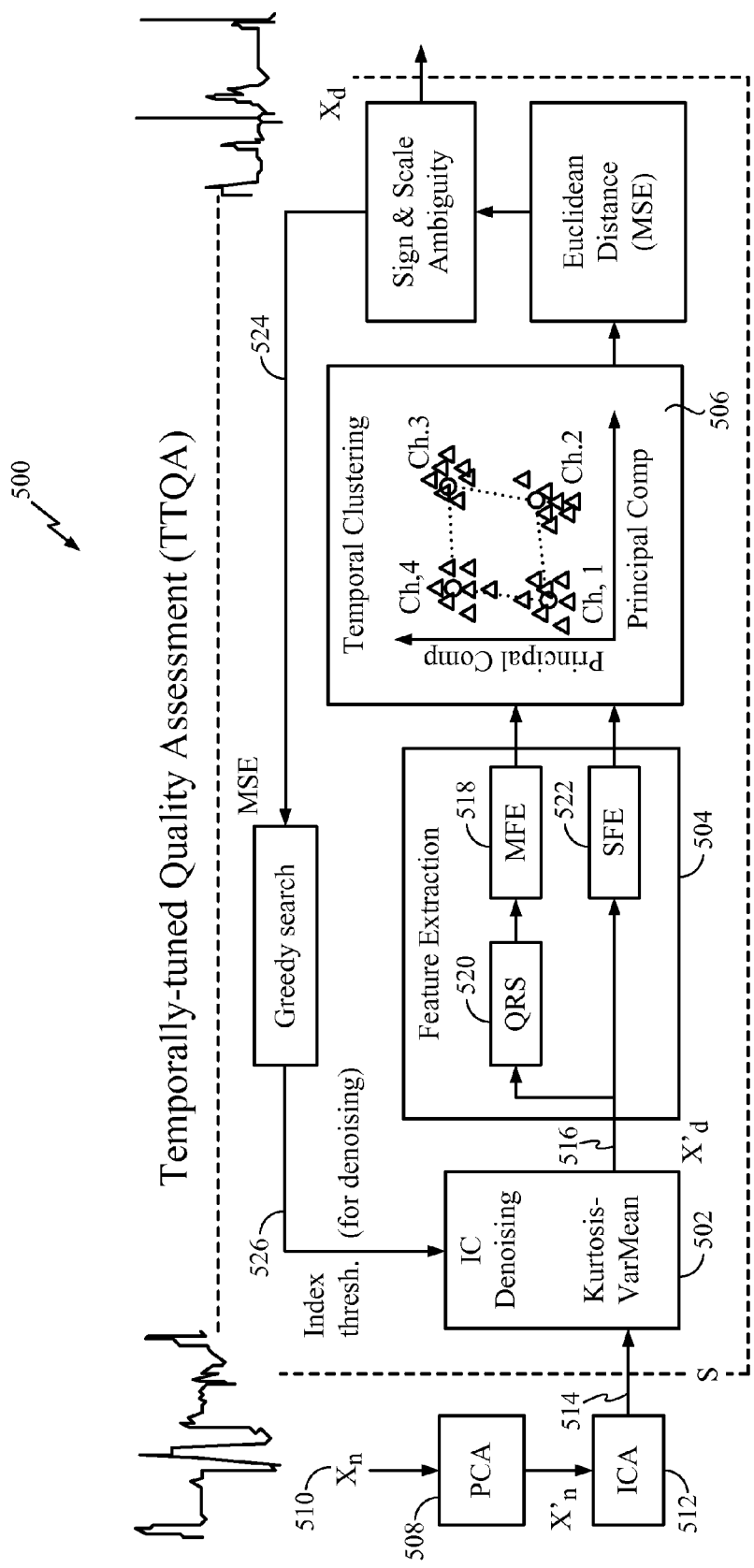
FIG. 5 illustrates an example block diagram of temporally tuned quality assessment (TTQA) technique in accordance with certain aspects of the present disclosure.

FIG. 5 illustrates an example block diagram 500 of an apparatus implementing the TTQA algorithm in accordance with certain aspects of the present disclosure. As illustrated in FIG. 5, the TTQA apparatus may comprise a module 502 for automatic identification of noise components based on a Kurtosis-VarMean metric, followed by a feature extraction module 504 and a module 506 for temporal clustering using spectral and morphological features of ECG data. For example, the extraction of morphological features may comprise detecting inflection points (peaks and valleys) of the ECG signal and determining a QRS complex based on the detected inflection points. In an aspect of the present disclosure, the acquisition circuits 102, 104, 106, 108 and/or the aggregator 110 from FIG. 1 may perform the TTQA along with the ICA illustrated in FIG. 5 for denoising of acquired physiological signals.

In an aspect, m frames of noisy recordings may be processed at a time corresponding to the in ECG leads. For example, a frame (e.g., the frame illustrated in the graph 402 in FIG. 4) may consist of four seconds of data from one lead and may comprise approximately four heart beats. A beat may be characterized by a QRS complex representing the electrical activity of the heart. FIG. 5 illustrates a signal 511 representing part of a noisy ECG recording from one frame, as well as a signal 513 that represent part of a denoised ECG signal from one frame.

Prior to denoising based on the TTQA, a unit 508 may apply a principal component analysis (PCA) on noisy data 510 (e.g., noisy ECG measurements) for dimensionality reduction based on orthogonal projection of the noisy data. Then, a unit 512 may apply the ICA for separating constituent ICs of the noisy data. If $f_s$ is a sampling frequency (having units of samples/second) of the noisy ECG data, m frames of $N \cdot f_s$ samples each (where N is a number of seconds), represented by x$_n$, may be processed at a time by the PCA block 508 ($N \cdot f_s$ samples from one frame 511 are illustrated in FIG. 5). After this, the ICA may be applied to separate k independent components in the noisy ECG data, which are represented by s in the example block diagram 500 of FIG. 5 (independent components 514 in FIG. 5).

In an aspect of the present disclosure, the TTQA apparatus from FIG. 5 may correspond to the wireless device 202 from FIG. 2. For example, the signal detector 218 may comprise the IC Denoising module 502, the PCA unit 508 and the ICA unit 512, and the processor 204 may comprise the feature extraction module 504 and the temporal clustering module 506.

The IC denoising block 502 may process the k independent components 514, wherein the IC denoising block 502 uses a Kurtosis-VarMean metric to enable automatic identification of noise components. Kurtosis is a fourth-order cumulant and it is zero for Gaussian densities. Kurtosis of the independent components s can be defined as:

$$K(s) = E(s^4) - 3[E(s^2)]^2. \quad (3)$$

where $E(\cdot)$ is the expectation operator.

A muscle noise having a near Gaussian distribution may have a Kurtosis value much smaller than an ECG signal and may thus be clearly distinguishable. However, although Kurtosis may be a useful metric to identify a continuous noise such as the muscle noise, a secondary measure may be needed for additional noise sources.

Figure 6:
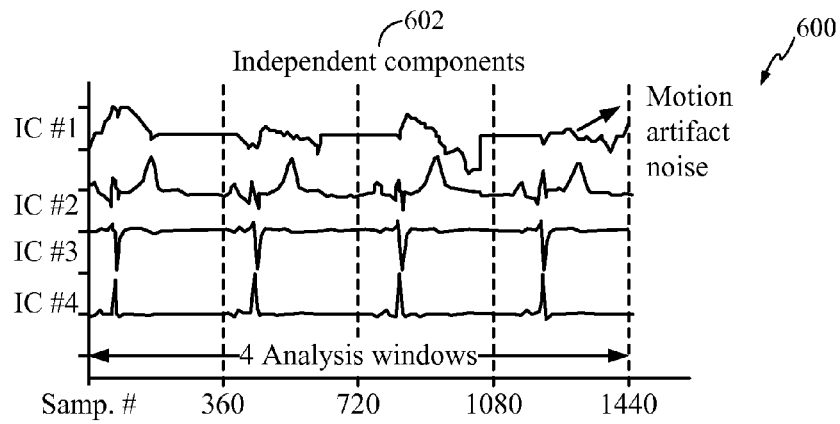
FIG. 6 illustrates examples of different statistical metrics applied for signal denoising in accordance with certain aspects of the present disclosure.
Figure 6:
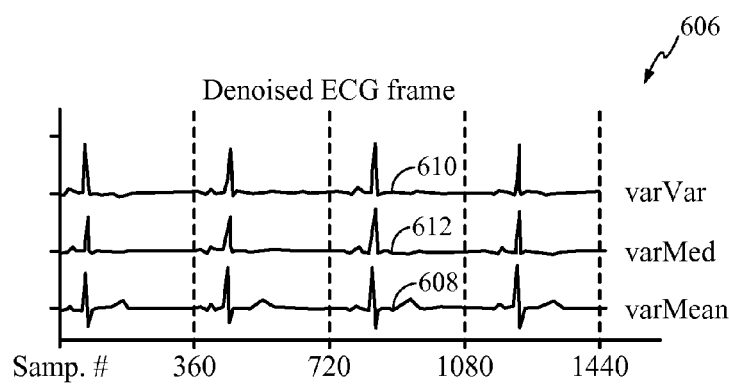

FIG. 6 illustrates an example 600 of different statistical metrics that may be applied for signal denoising in accordance with certain aspects of the present disclosure. A graph 602 in FIG. 6 shows four ICs separated using the ICA, wherein a motion artifact may be the only noise component present (IC #1 component in the graph 602) and the other components may be signals (IC #2, IC #3, and IC #4).

For every component $s_i$ of $N \cdot f_s$ samples obtained using m ECG leads, VarMean may correspond to a variance in a mean amplitude of N linearly spaced windows (e.g., one-second windows). In other words, suppose $s_{it}'$ and $\bar{s}_{it}'$ represent a segment of $f_s$ samples derived from $s_i$ before time $t \in 1, 2, \ldots, N$ and its mean amplitude, respectively. The VarMean corresponds to the variance of the set $y_i = \{\bar{s}_{i1}', \bar{s}_{i2}', \ldots, \bar{s}_{iN}'\}$. The VarVar and VarMed are related metrics in which $\bar{s}_{it}'$ corresponds to the variance and median of $s_{it}'$, respectively.

As illustrated in Table 604 in FIG. 6, the VarVar metric may be ineffective for identification of the electrode motion noise. By using the VarVar metric, values of Kurtosis-VarVar index (defined as a ratio of Kurtosis and VarVar values) for both IC #1 (noise) and IC #2 (ECG signal) are below threshold, and are treated as noise though IC #2 is not noise. It should be also noted that Kurtosis-VarVar index for IC #1 (noise) is greater than Kurtosis-VarVar index for IC #2 (ECG signal). Therefore, the use of Kurtosis-VarVar index may lead to faulty elimination of signal component IC #2 by greedy thresholding. Motion artifacts may appear as sporadic events and their VarVar value cannot always be efficiently distinguished from that obtained using components associated with the ECG signal. Thus, new metrics of VarMed and VarMean are evaluated that exploit the quasi-periodic nature of the ECG signal components. In contrast to VarVar metric, Kurtosis-VarMed index (ratio of Kurtosis and VarMed values) for IC #2 (ECG signal) is greater than Kurtosis-VarMed index for IC #1 (noise), and only Kurtosis-VarMed index for IC #1 is below the threshold. Using the Kurtosis-VarMean index (ratio of Kurtosis and VarMean values) further distances IC #1 from IC #2, and again only the Kurtosis-VarMean index for IC #1 is below the threshold. The SINR increases for both VarMean and VarMed metrics because IC #2 is treated as signal for these measurements rather than noise.

As illustrated in Table 604 in FIG. 6, VarMean values of ECG signal components may be smaller than that obtained from motion artifacts occurring at irregular intervals. This is expected since the mean amplitudes in adjacent windows $\bar{s}_{it}'$ derived from the quasi-periodic ECG signal components can be close to each other. The denoising index (i.e., the ratio of Kurtosis and VarMean, $K(s)/\sigma_y^2$) may thus enable the accurate distinction of motion artifact and muscle noise components from those that correspond to the ECG signal source. A graph 606 in FIG. 6 illustrates a denoised ECG frame 608 when the Kurtosis-VarMean metric is used for denoising. This frame is also compared with denoised ECG frames 610, 612 when the VarVar and VarMed based indices are utilized for denoising, respectively. It should be noted the secondary hump (contributed by IC #2) that pops up in the frame 608 where the Kurtosis-VarMean index is applied for denoising, which is not present in the 610, 612 frames.

A modified demixing matrix $\tilde{W}^1$ of reduced rank k' for denoising of k independent components (e.g., the independent components 514 from FIG. 5) may be thus obtained by zeroing out k-k' columns (components) corresponding to the noise components identified by their $K(s)/\sigma_y^2$ index being below a certain threshold. After one iteration of the threshold-based denoising, in ECG frames of $N \cdot f_s$ samples each, represented as $x_d'$ may be thus obtained using the signal components according to equation (2). Referring back to FIG. 5, the IC denoising unit 502 may zero out k-k' noise components of the independent components 514 to obtain a denoised signal 516 (e.g., denoised ECG data).

The denoised signal 516 may be further processed for dimensionality reduction. In one aspect of the present disclosure, a unit 518 of the feature extraction module 504 may perform morphological feature extraction (MFE) on the denoised ECG signal 516 to obtain a feature vector of the ECG data. In this case, a QRS detector 520 may identify the location of fiducial points in the denoised ECG signal 516, and the feature vector may be obtained using the average morphology of the denoised ECG signal represented by $f_s/3$ samples around each heart beat. In another aspect of the present disclosure, a unit 522 of the feature extraction module 504 may perform spectral feature extraction (SFE) on the denoised ECG signal 516, where a feature vector may be, for example, represented by the energy content in 16 linearly spaced spectral bins with a cumulative bandwidth of $f_s/2$.

Following the feature extraction process, the module 506 may perform temporal clustering to assess quality of the denoised ECG signal in a current iteration. It should be noted that the morphology and spectral content of an ECG signal may vary gradually in time. Thus, in an aspect, the $i^{th}$ denoised signal frame of N seconds may be correlated with the $(i-1)^{th}$ denoised frame for each of the m ECG channels. This may provide a local signal-dependent metric for the automatic quality assessment of the denoised ECG. A feature vector derived from the $(i-1)^{th}$ frame may thus constitute a global centroid $f_{d,GC}^i$. It should be noted that, in the initialization phase, a calibration centroid $f_{d,CAL}$ may be used for $f_{d,LC}^i$. Further, if the local centroid for the $i^{th}$ frame corresponds to a feature vector $f_{d,LC}^i$, a mean square error (MSE) 524 in FIG. 5 may be characterized by a Euclidean distance between $f_{d,GC}^i$ and $f_{d,LC}^i$. The MSE 524 may be minimized by updating (based on the current MSE value) an index threshold 526 (e.g., the $K(s)/\sigma_y^2$ threshold) that efficiently eliminates the noise components in a greedy search loop in subsequent iterations. Hence, the minimum mean square error (MMSE) solution for the centroids may constitute the best possible set of signal components in the current denoised frame.

The following provides an example pseudo-code of the self-sustaining TTQA algorithm in accordance with certain aspects of the present disclosure. The TTQA may need that $N \geq 2 f_s$, and the calibration centroid $f_{d,CAL}$ may be set to zero. The TTQA may ensure the MMSE solution for the global and local centroids, i.e., it may minimize $\|f_{d,GC} - f_{d,LC}\|^2$.

In the initialization phase, the ICA algorithm may be applied to obtain a set of ICs, i.e., $S \leftarrow ICA(X_s)$. In addition, $f_{d,CAL} = f_{d,CAL}$, and MMSE may be set to infinity (or some large value). A sorted index list L may be created based on the $K(S)/\sigma_y^2$ indices of all ICs in the set S.

For each component j in the sorted list L, the denoising may be performed and the updating of global centroid. First, $\tilde{W}^{-1} \leftarrow 0$, for all components in L that satisfy $L < L(j)$, and $X_d' := \tilde{W}^{-1} S$. Following this, a value of local centroid $f_{d,LC}^i$ may be obtained by performing the SFE or the MFE on the denoised signal $X_d'$. Then, the Euclidean distance (i.e., MSE) between $f_{d,GC}^i$ and $f_{d,LC}^i$ may be computed. If MSE<MMSE, then $X_d \leftarrow X_d'$; MMSE$\leftarrow$MSE; and $f_{d,GC}^i \leftarrow G(f_{d,LC}^i)$, wherein G is a transformation function used to update the global centroid and will be later defined.

Experimental Results

The MIT-BIH NST (Massachusetts Institute of Technology—Beth Israel Hospital Noise Stress Test) database provides typical recordings of baseline-wander, electrode motion and muscle noise in an ambulatory ECG. For simulation purpose, a calibrated amount of these noise sources is added to 549 records of 12 lead 1 kHz ECG data from 249 subjects of the PTB database.

Figure 7:
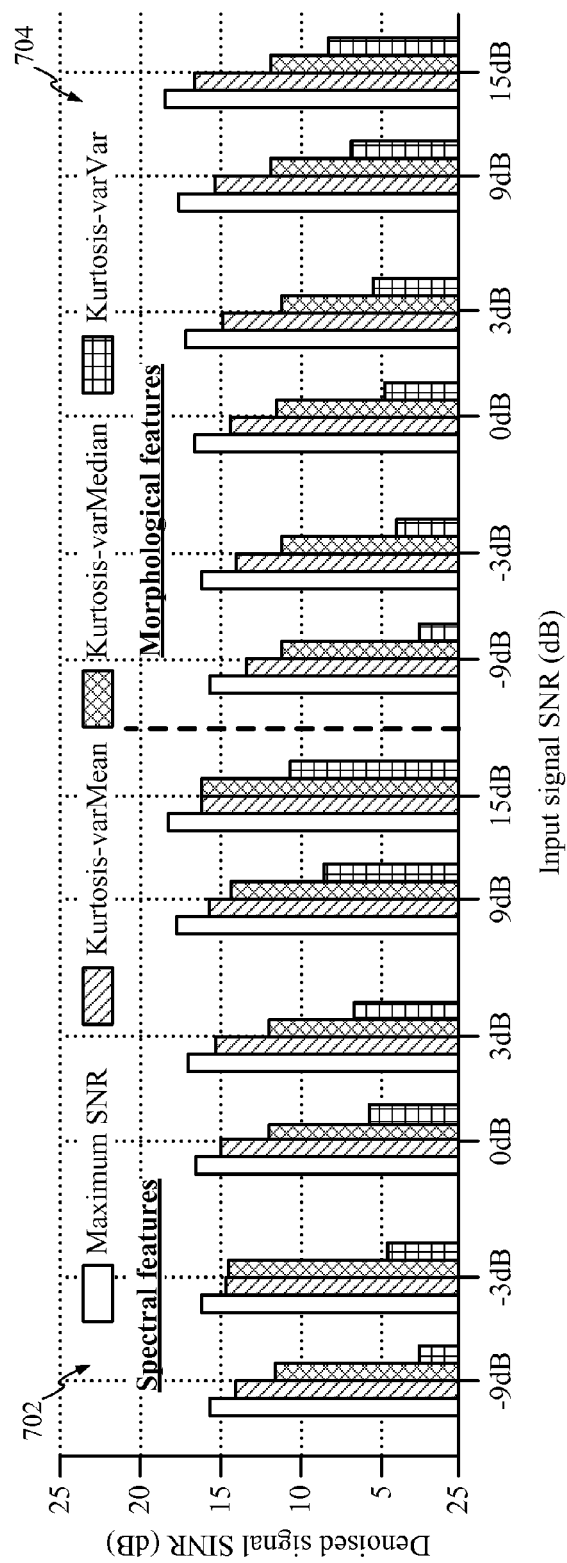
FIG. 7 illustrates example graphs of denoised signal signal-to-interference-plus-noise ratio (SINR) for TTQA based denoising with Kurtosis-VarMean, Kurtosis-VarVar and Kurtosis-VarMedian metrics in accordance with certain aspects of the present disclosure.

FIG. 7 illustrates example graphs 702 and 704 of a denoised signal SINR for TTQA based denoising across a range of an input signal SNR in accordance with certain aspects of the present disclosure. The graph 702 corresponds to the TTQA based denoising with extraction of spectral features, while the graph 704 corresponds to the TQA based denoising with extraction of morphological features. The SINR can be defined as $10 \log[P(x_e)/P(x_d-x_e)]$, where $x_e$ is an expected ECG signal available from the PTB database, $x_d$ is a denoised ECG signal obtained by applying the iterative TTQA with ICA, and $P(\cdot)$ represents a power of a signal. It can be observed from FIG. 7 that Kurtosis-VarMean based denoising may achieve SINR values close to that attainable by denoising the independent components using a brute force search (i.e., maximum SNR based denoising) that has much higher computational and implementation complexity than the Kurtosis-VarMean based denoising. It can also be observed from FIG. 7 that the Kurtosis-VarMean based denoising is more robust than that based on Kurtosis-VarVar and Kurtosis-VarMedian thresholds.

Figure 8:
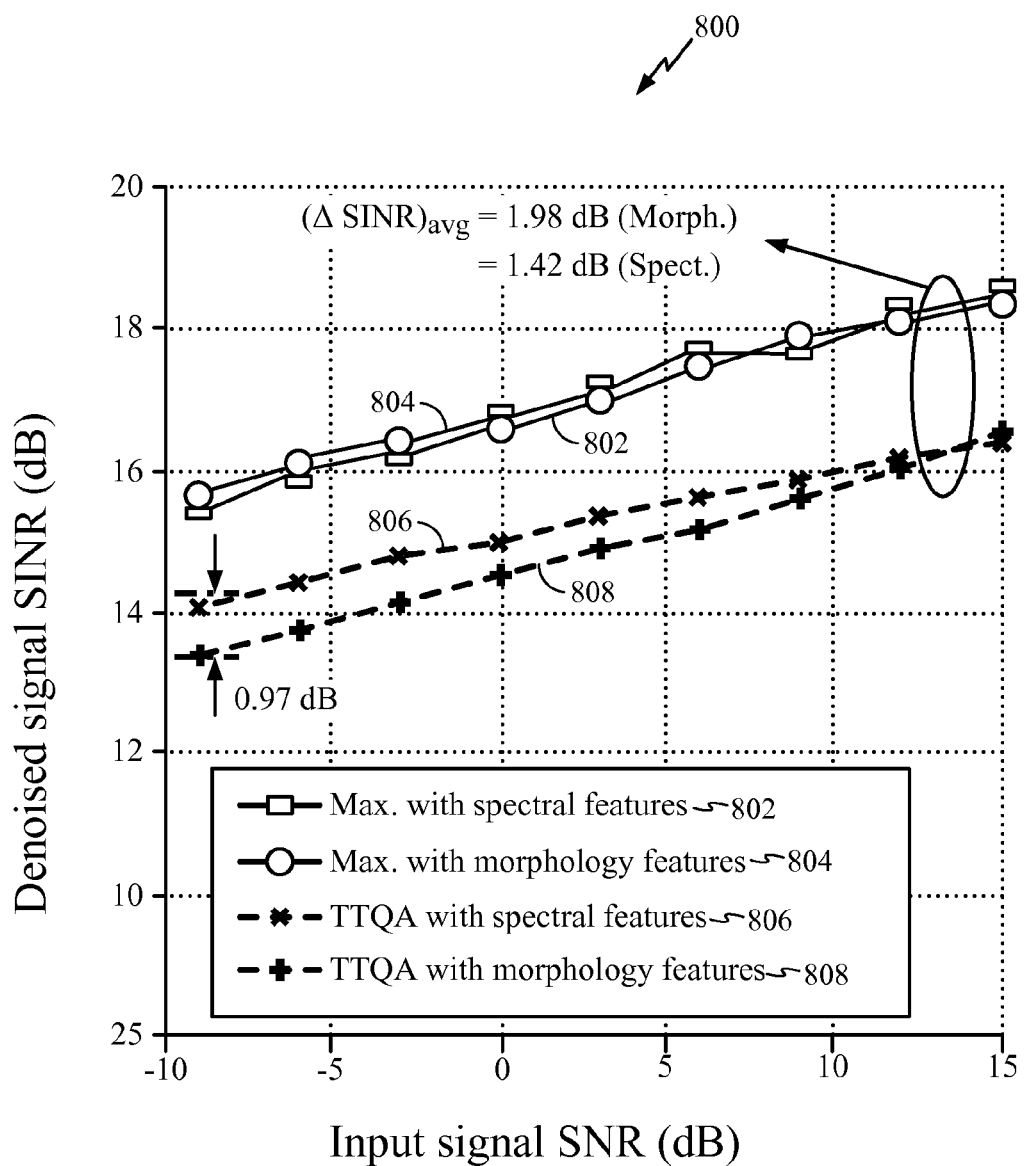
FIG. 8 illustrates example graphs of denoised signal SINR for TTQA based denoising with morphological feature extraction (MFE) and spectral feature extraction (SFE) in accordance with certain aspects of the present disclosure.

FIG. 8 illustrates an example graph 800 showing a denoised signal SINR performance of the TTQA based denoising of ECG data from the PTB database across a wide range of input signal SNR values in accordance with certain aspects of the present disclosure. It can be observed from FIG. 8 that TTQA with WE (a plot 808 in FIG. 8) and TTQA with SFE (a plot 806 in FIG. 8) show similar denoising performance. It can be also observed from FIG. 8 that the denoising algorithm may be almost insensitive to the input signal SNR since the property of statistical independence is valid even in the presence of large amplitudes of noise. FIG. 8 also illustrates that the greedy search in TTQA may compare well with a maximum attainable SINR using a brute force search (the TTQA plots 806 and 808 vs. brute force search plots 802 and 804).

Figure 9:
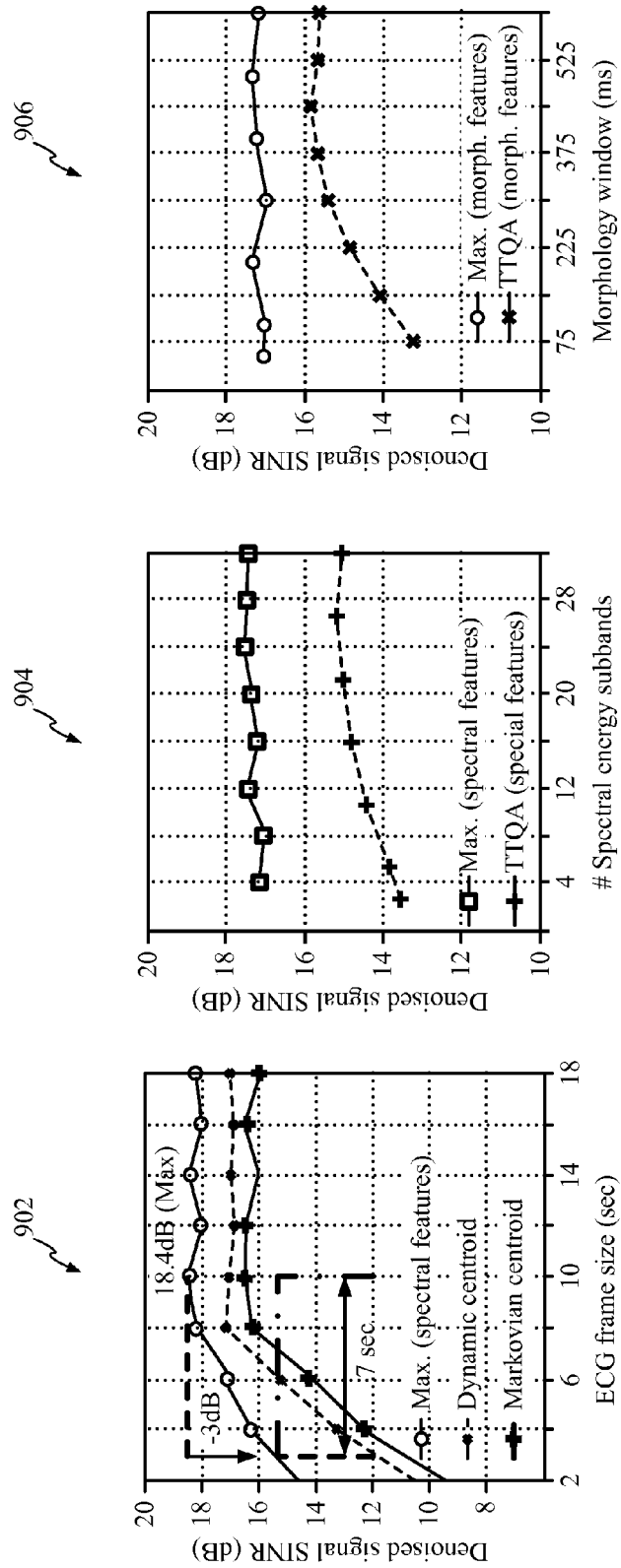
FIG. 9 illustrates example graphs showing how increasing a signal frame size where denoising is applied and increasing spectral/temporal resolution of feature extraction affect denoising efficiency in accordance with certain aspects of the present disclosure.

FIG. 9 illustrates the effect of scaling the analysis parameters in TTQA in accordance with certain aspects of the present disclosure. It can be observed from a graph 902 that increasing a size of an analysis frame beyond 10 seconds may saturate the SINR gains. Further, increased spectral resolution by the use of a larger number of spectral energy bins may not improve the denoising efficiency, as being illustrated in a graph 904 in FIG. 9. A similar behavior of diminishing returns can be observed with increased temporal resolution of the morphological features by the use of a larger number of samples around the fiducial points for $f_{d,LC}^{i}$, as being illustrated in a graph 906 in FIG. 9.

In the previously described temporal clustering of the TTQA denoising, a strategy used for the global centroid update may impact the denoising efficiency. In an aspect, when processing the $i^{th}$ frame, the global centroid $f_{d,GC}^{i}$ may be updated using a transformation applied to the local centroid $f_{d,LC}^{i}$ in that frame. One of the following three strategies (transformations G) can be used for the global centroid update in the TTQA:

$$f_{d,GC}^{i} = G(f_{d,LC}^{i}) = \begin{cases} f_{d,LC}^{i}, & \text{if Markovian,} \\ f_{d,CAL}, & \text{if static,} \\ \left(\sum_{i=1}^{F} f_{d,LC}^{i}\right)/F & \text{if dynamic,} \end{cases} \quad (4)$$

The Markovian centroid may assign the local centroid of the current frame to the global centroid of the next frame. This may have a poor denoising performance since a sub-optimally denoised frame may lead to a cascade of sub-optimally denoised frames. In the case of static centroid, a calibration frame (a cold-start frame during which there are no artifacts in the measured ECG) may be used as a static template. Although this strategy may overcome the problem of error-propagation, it may not capture the evolving patient physiology. Thus, the TTQA may employ a dynamic centroid where the global centroid is assigned to be the average of the local centroids from the previous F frames, as given in equation (4).

Figure 10:
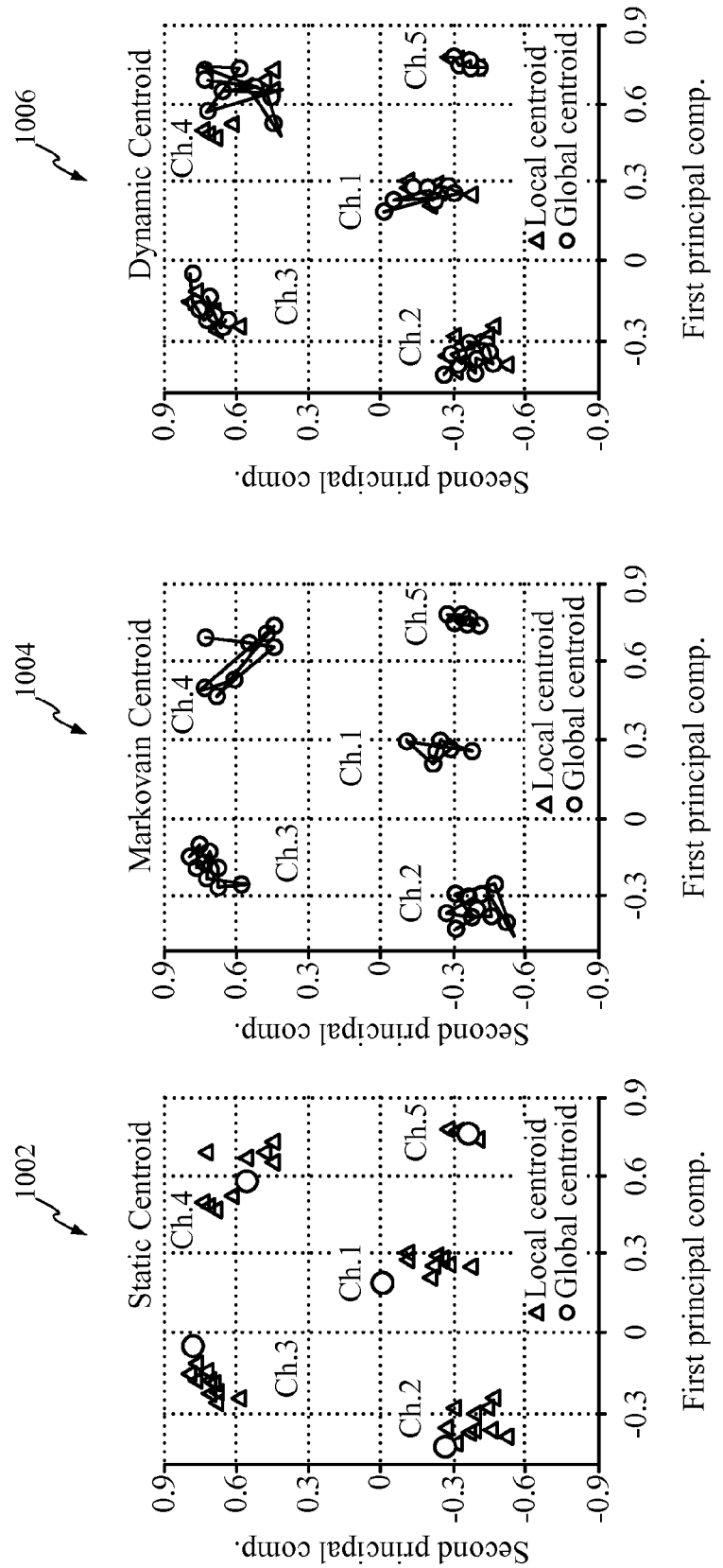
FIG. 10 illustrates example graphs of static, Markovian, and dynamic centroids that may be utilized in a temporal clustering of TTQA based denoising in accordance with certain aspects of the present disclosure.

FIG. 10 illustrates example graphs of locations of static, Markovian, and dynamic centroids that may be utilized in the temporal clustering of the TTQA based denoising in accordance with certain aspects of the present disclosure. By comparing graphs 1002, 1004, and 1006, it can be observed that Euclidean distances between global and local centroids are smallest in the case of dynamic centroid approach defined in equation (4). Therefore, the dynamic centroid approach may provide smallest MSE values 524 in the TTQA denoising block diagram 500 illustrated in FIG. 5.

Figure 11:
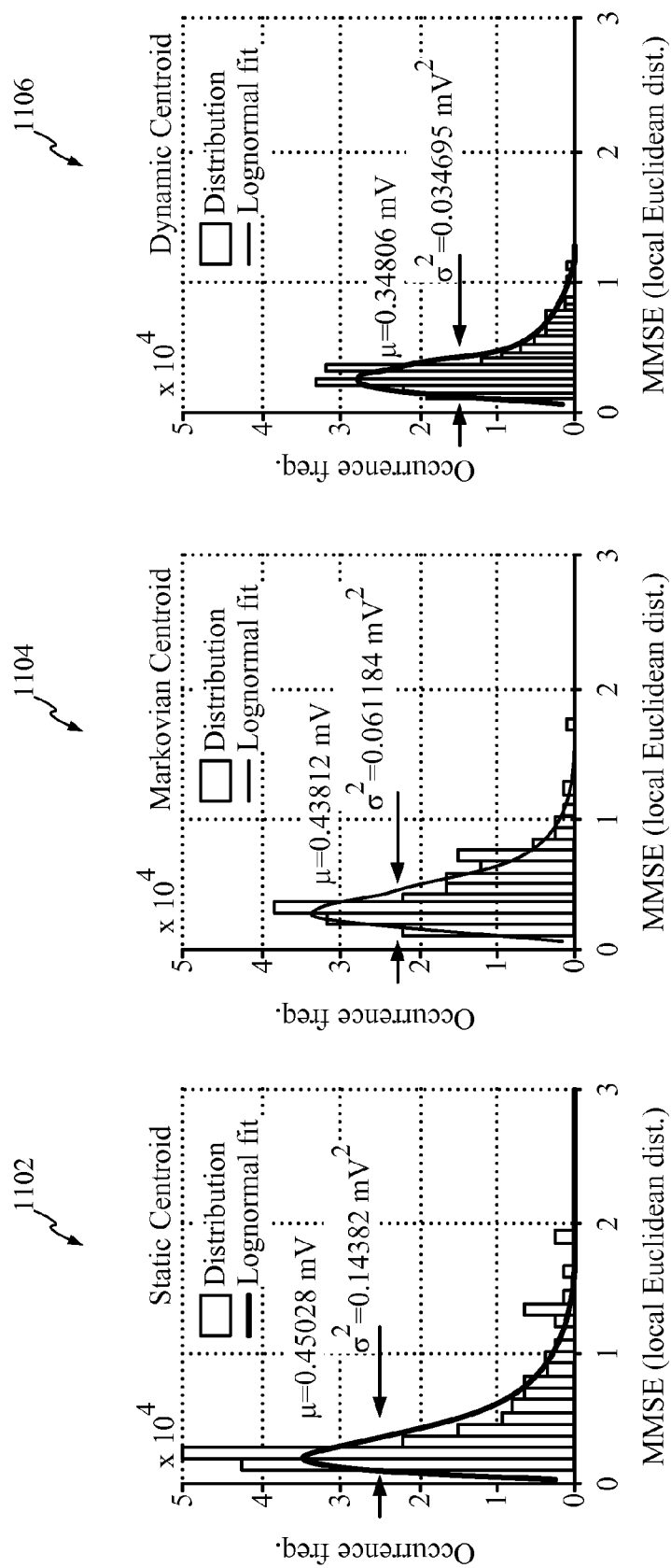
FIG. 11 illustrates example graphs of minimum mean square error (MMSE) performance of TTQA based denoising when static, Markovian, and dynamic centroids are utilized in a temporal clustering in accordance with certain aspects of the present disclosure.

FIG. 11 illustrates example graphs of MMSE performance of the TTQA based denoising across 0.6 million ECG frames of four seconds each from the PTB database when static, Markovian, and dynamic centroids are utilized in the temporal clustering in accordance with certain aspects of the present disclosure. It can be observed from graphs 1102 (MMSE performance in the case of static centroid), 1104 (MMSE performance in the case of Markovian centroid) and 1106 (MMSE performance in the case of dynamic centroid) that the dynamic centroid based update results in a smallest mean MMSE of 0.35 mV. This represents improvements of 25.9% and 29.4% over using the Markovian and static centroids, respectively. A smaller variance in the MMSE is also observed in the case of dynamic centroid, as illustrated in the graph 1106 in FIG. 11.

Arrhythmia Classification and Beat Detection

In the present disclosure, the ability of TTQA to accurately denoise ECG signals by preserving a patient physiology using a case study of arrhythmia detection is analyzed. FIG. 12 illustrates an example 1200 of arrhythmia classification and beat detection with strong resilience to a noise after TTQA based denoising in accordance with certain aspects of the present disclosure. The evaluation presented in FIG. 12 is based on the American Hospital Association (AHA) database. The performance of the beat detection algorithm is presented according to the ANSI/AAMI EC57 specification standard. The sensitivity in the classification of normal (Q Se) and ventricular ectopic beats (V Se) is 99.78 and 93.43%, respectively. The corresponding positive predictivity (+P) values are 99.87% and 98.5%, respectively. The data in FIG. 12 also shows the false positive rate (V FPR) along with the total number of ventricular ectopic beats (VEB) identified by the arrhythmia detection software in the AHA database.

It can be observed from a row 1202 in FIG. 12 that the use of TTQA on the AHA database prior to the application of the Mortara software did not significantly improve the detection performance. However, when the noise from the MIT-BIH NST database was added to the AHA database, the detection accuracy of the classification algorithm suffered heavily. FIG. 12 shows degradation in the detection performance for input signal SNR values of −9 dB, −3 dB, 0 dB, +3 dB and +9 dB. However, arrhythmia classification using TTQA denoised ECG showed significant improvement in the performance of the detector. The corresponding results for arrhythmia detection for various input SNR values after TTQA, are also shown in FIG. 12 (columns 1204, 1206 with V FPR and VEB results). Thus, TTQA may enable an automatic identification of noise components and a closed-loop quality assessment of the denoised ECG while accurately preserving pathological conditions in the evolving patient physiology.

Instantaneous Heart Rate Estimation

Figure 13:
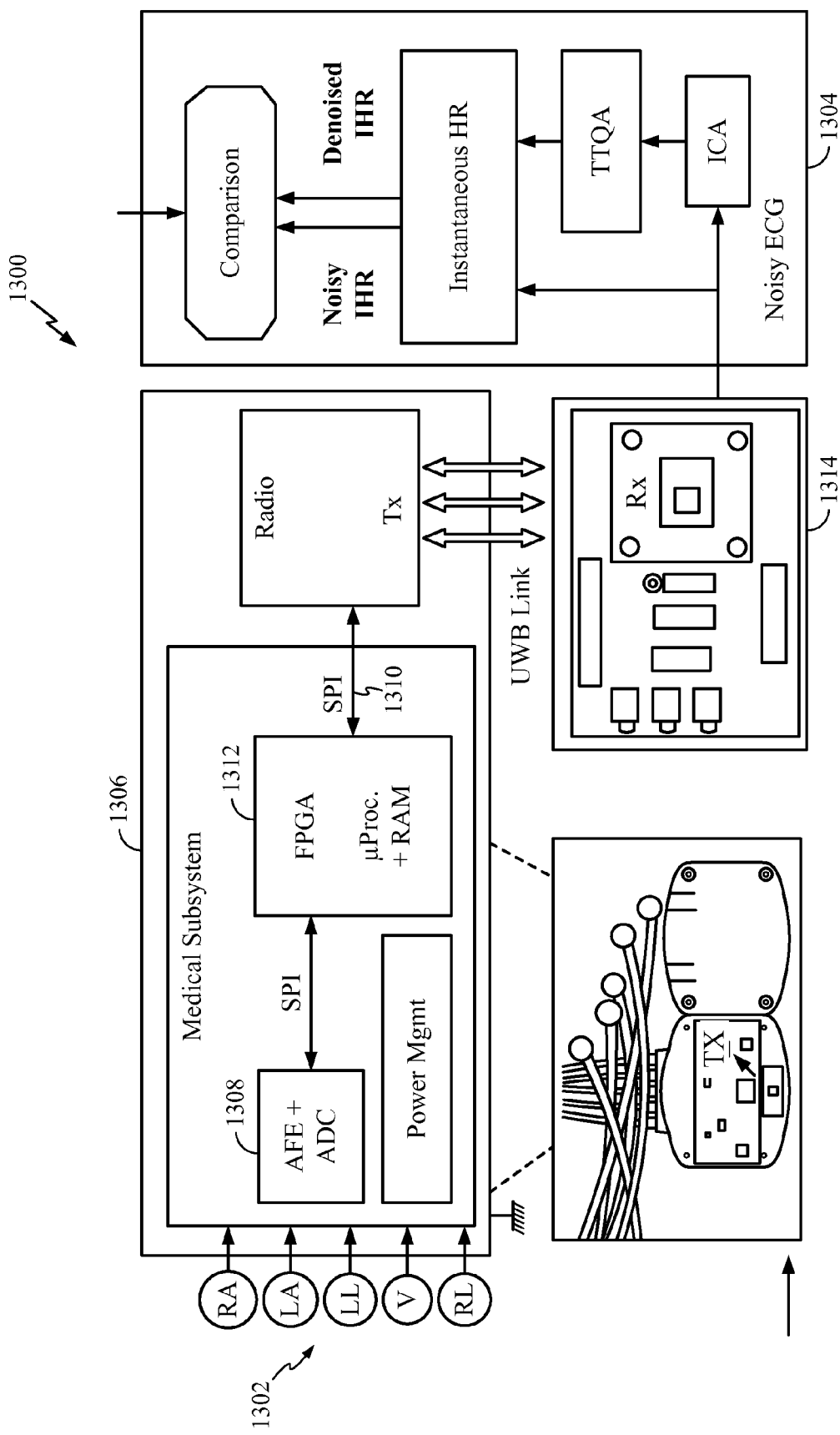
FIG. 13 illustrates an example of instantaneous heart rate (IHR) estimation in accordance with certain aspects of the present disclosure.
Figure 14A:
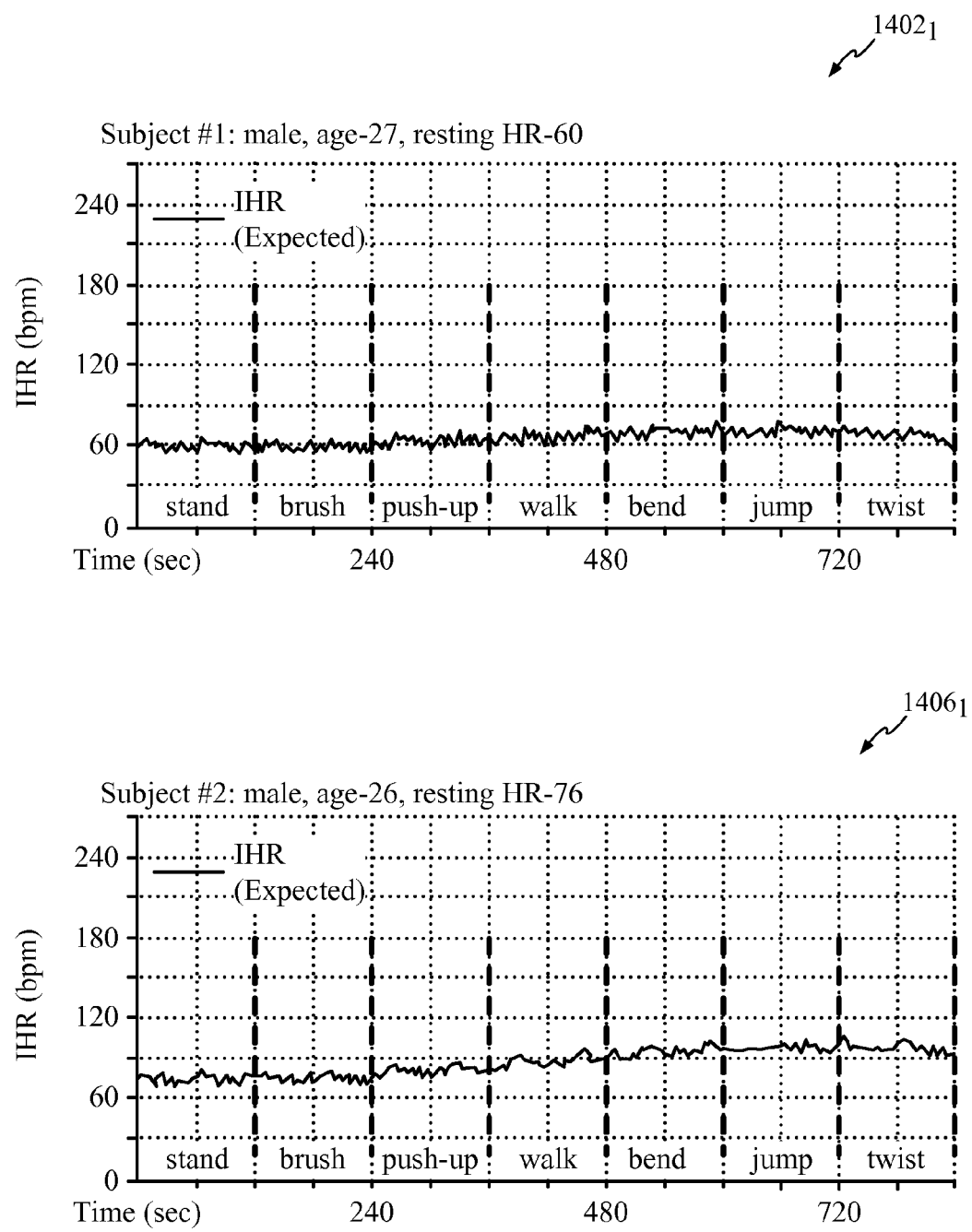
FIGS. 14A-14F illustrate an example of measurements and estimates of IHR from four subjects performing routine activities in accordance with certain aspects of the present disclosure.
Figure 14B:
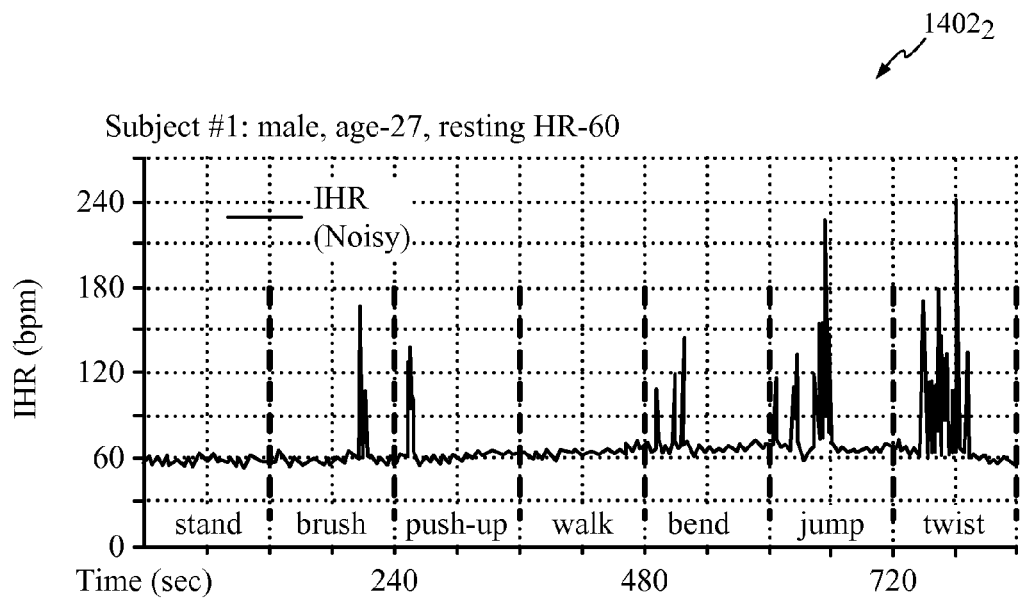
Figure 14B:
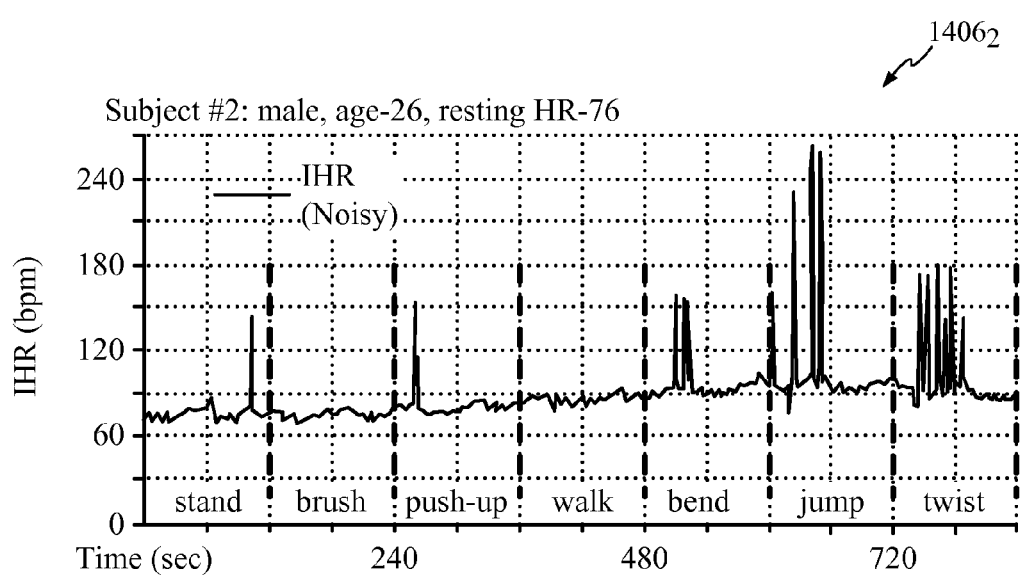
Figure 14C:
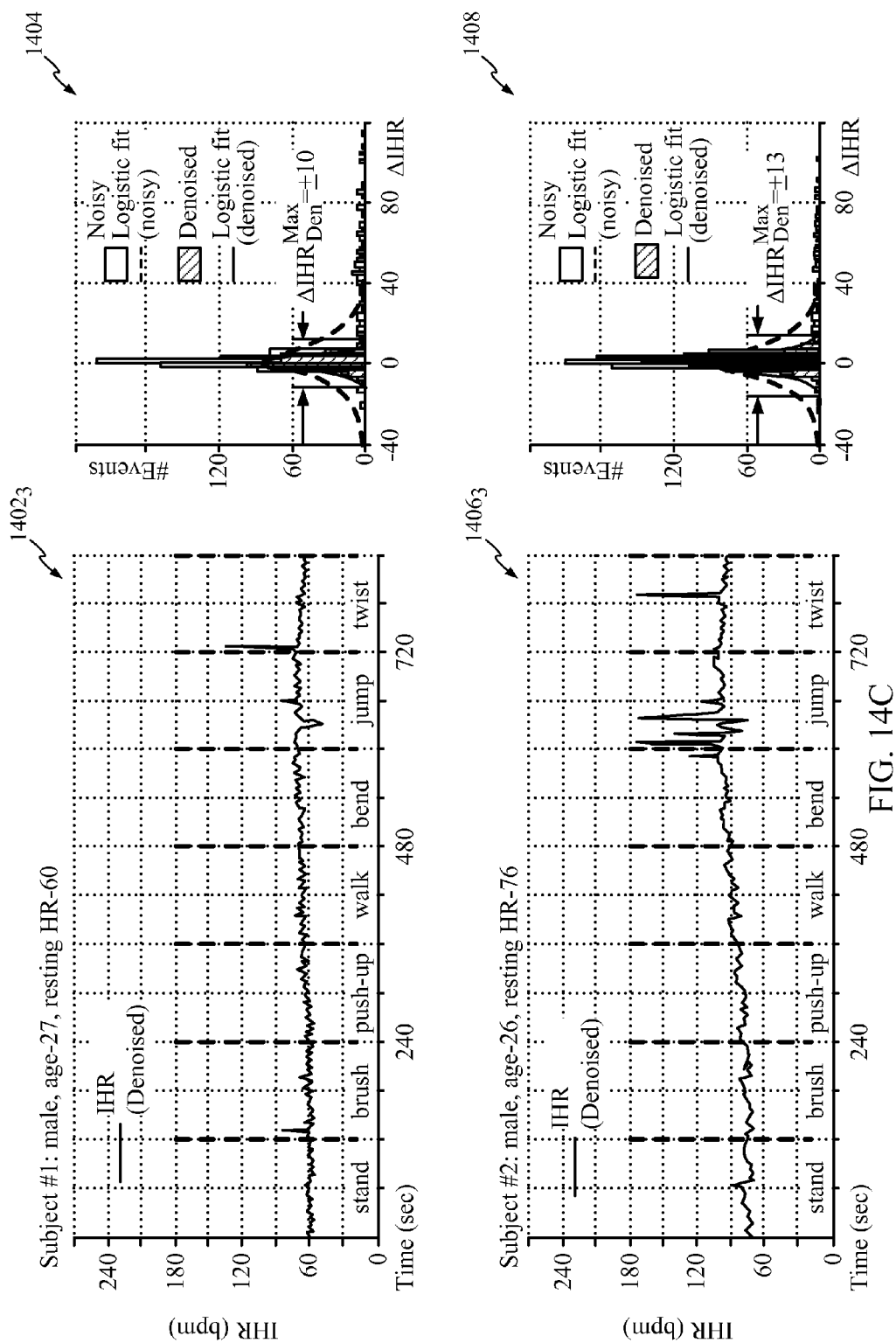
Figure 14D:
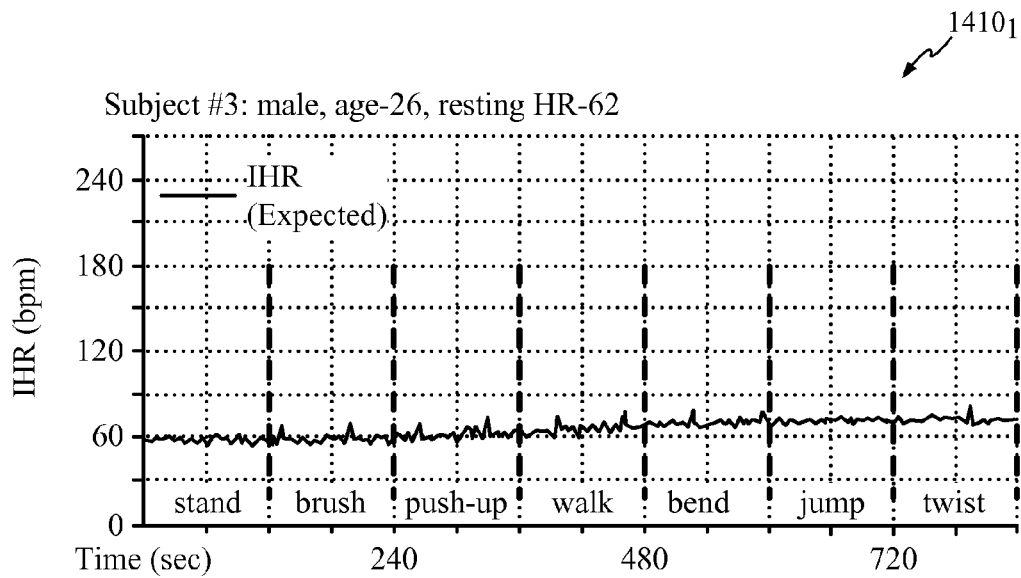
Figure 14D:
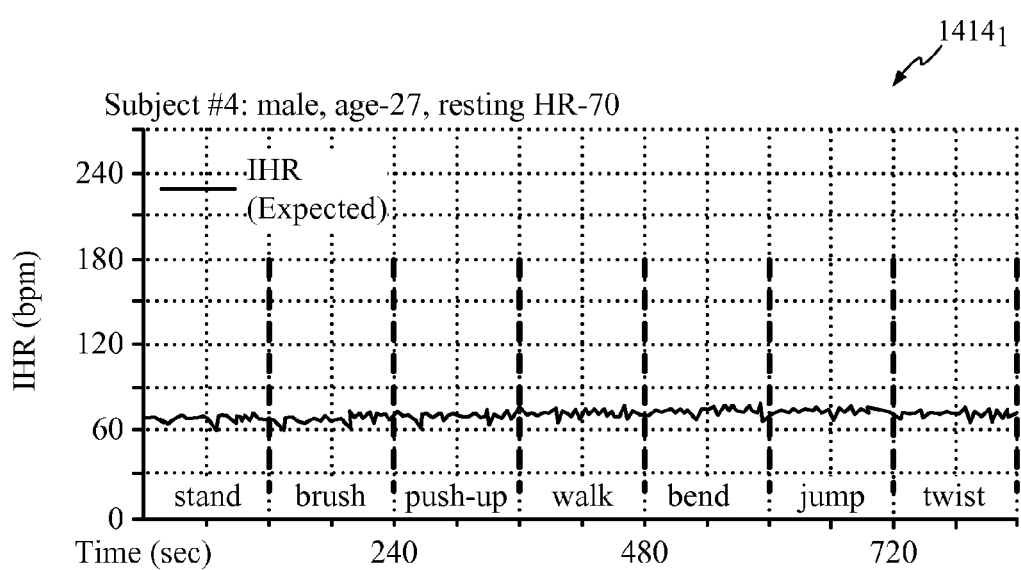
Figure 14E:
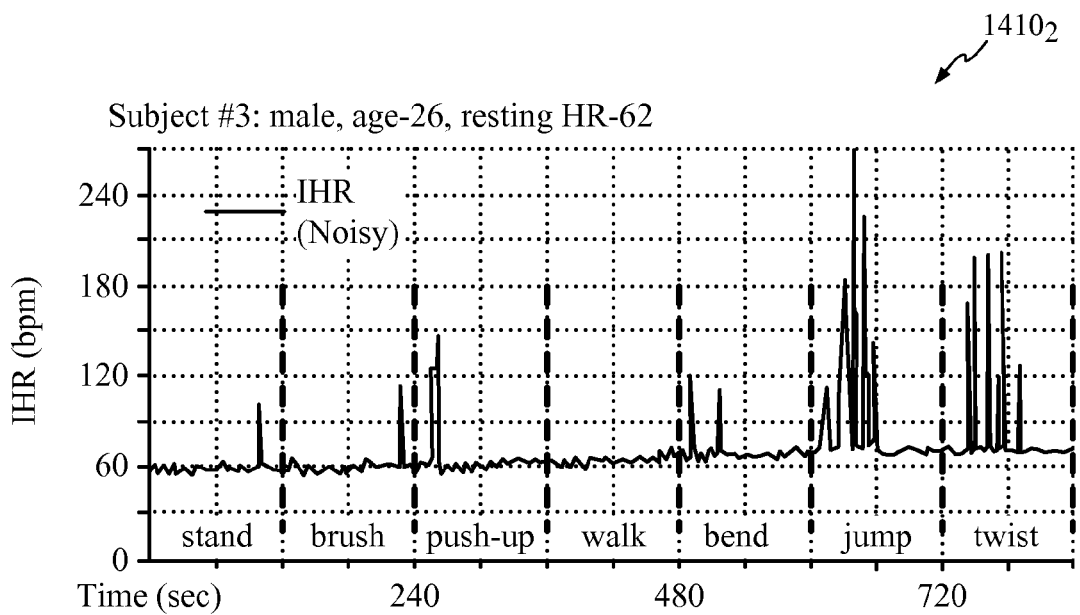
Figure 14E:
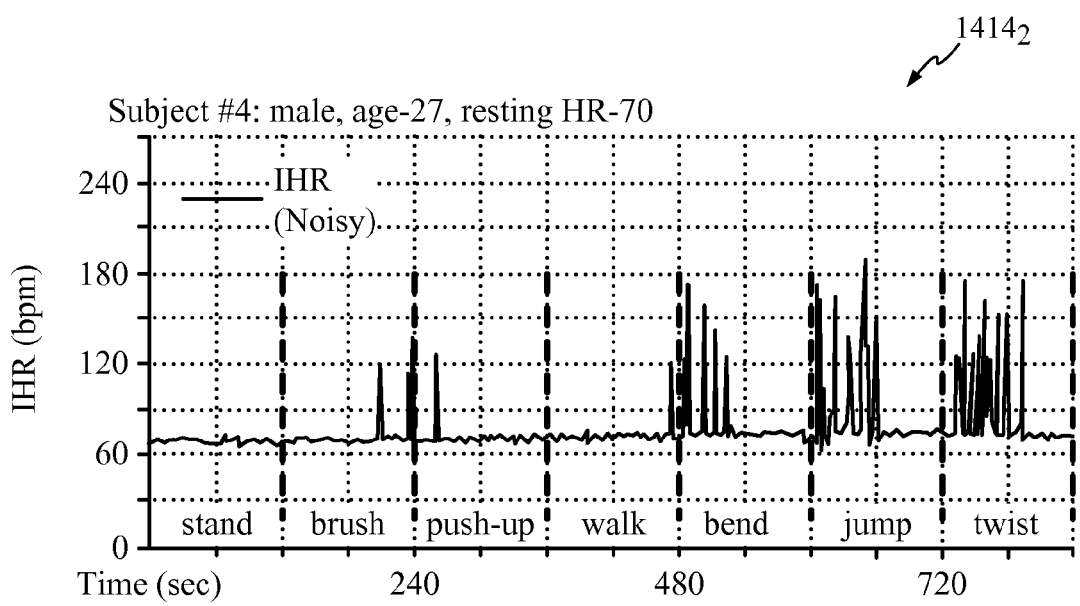
Figure 14F:
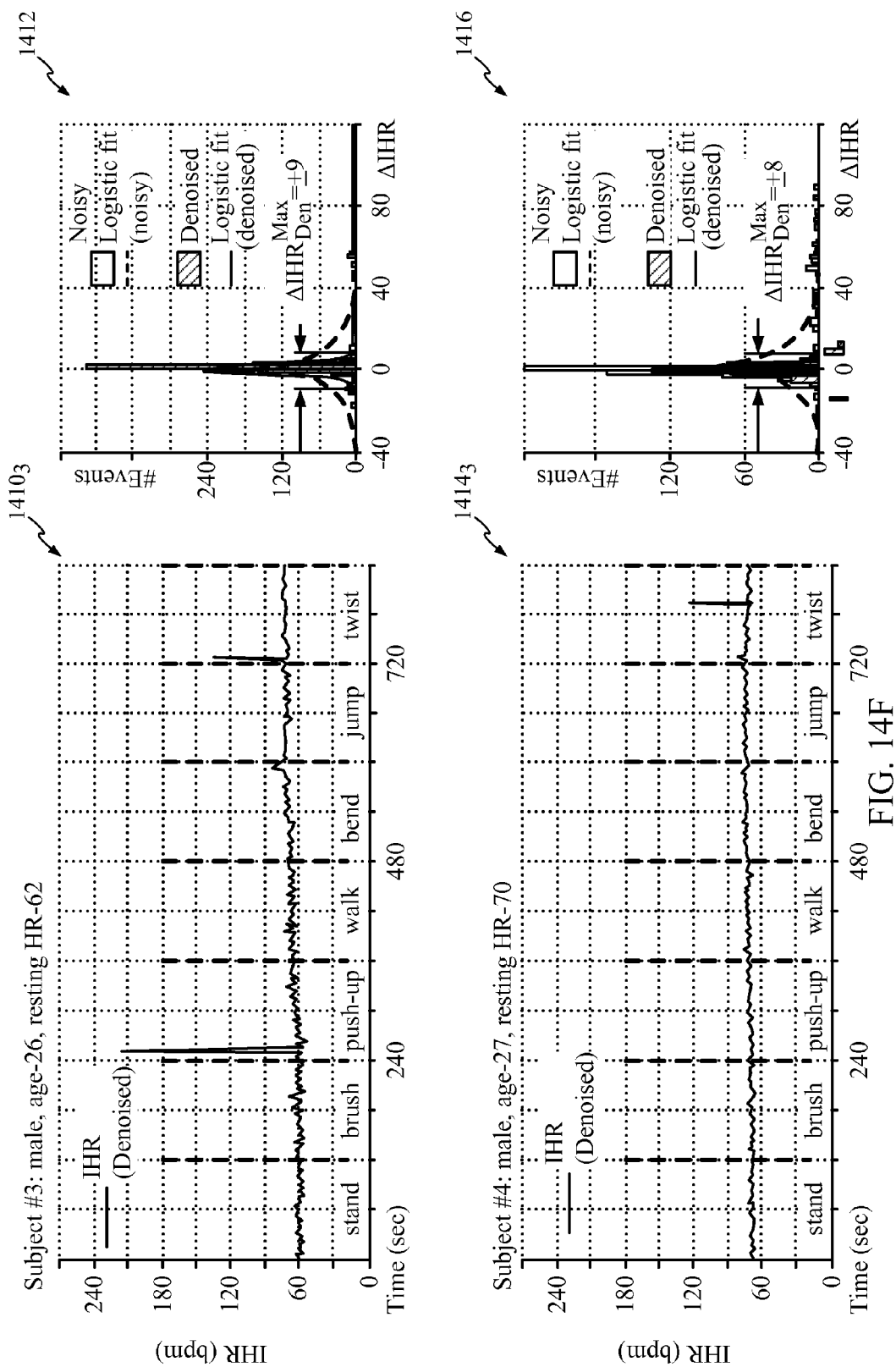

In all experiments with the PTB and AHA databases, a synthetic noise was added from the MIT-BIH NST database to create the noisy ECG signals. In this section, another more realistic case-study of IHR measurements using ECG recordings from subjects performing routine activities is described. Thus, no artificial noise was added to the ECG signals. FIG. 13 illustrates an example 1300 of a system diagram of a platform used for evaluation of the TTQA based denoising with ICA.

A five-lead ECG 1302 was measured from four subjects and communicated to a processing unit 1304, e.g., transmitted over a proprietary ultra-wide-band (UWB) radio link. As illustrated in FIG. 13, a medical sub-system 1306 of a sensor platform may comprise an analog frontend (AFE) and an Analog-to-Digital Convertor (ADC) 1308. Digitized samples 1310 may be transmitted at 500 Hz and 16-bits of resolution. An on-board Actel Igloo Field Programmable Gate Array (FPGA) 1312 (with a microprocessor and a Random Access Memory (RAM)) may enable Media Access Control (MAC) packetization and efficient encoding for secure communication. A receiver test board 1314 may be connected to the processing unit 1304 for performing the TTQA based denoising with ICA.

A pulse rate monitor device may be employed for measuring the expected IHR of subjects performing routine activities. In an aspect of the present disclosure, the expected IHR can be compared against the IHR computed with the direct use of noisy ECG as well as that computed with the use of TTQA denoised ECG. The IHR computation may comprise QRS detection. The resulting distance between the fiducial points (RR-interval) can be used to compute the IHR as follows: IHR=60/RR-interval in seconds.

FIGS. 14A-14F illustrate the IHR measurements and estimates using noisy ECG and TTQA denoised ECG from four subjects with no pathological condition. In this example, each subject performs seven routine tasks for 60 seconds preceded by 60 seconds of inactivity, as illustrated in graphs $1402_1$-$1402_3$, $1406_1$-$1406_3$ in FIGS. 14A-14C, and in graphs $1410_1$-$1410_3$, $1414_1$-$1414_3$ in FIGS. 14D-14F. Histograms 1404, 1408, 1412, 1416 of all four subjects show distribution of an error in the estimated IHR as compared to the measured IHR using the pulse monitor. As it is observed from IHR graphs $1402_3$, $1406_3$, $1410_3$, $1414_3$ and histograms 1404, 1408, 1412, 1416 in FIG. 14C and FIG. 14F, TTQA denoised ECG enables accurate IHR estimation with an average upper bound of ±10 bpm ($\Delta IHR_{Den}^{Max}$) as compared to ±52 bpm with the direct use of noisy ECG ($\Delta IHR_{Noi}^{Max}$). The root mean square (RMS) error in the IHR estimation after the TTQA is given in FIG. 15 for all four subjects showing an improvement of average accuracy from 47.7% to 7.0%. This validates the ability of TTQA to enable accurate artifact mitigation in multi-lead ECG.

Figure 16:
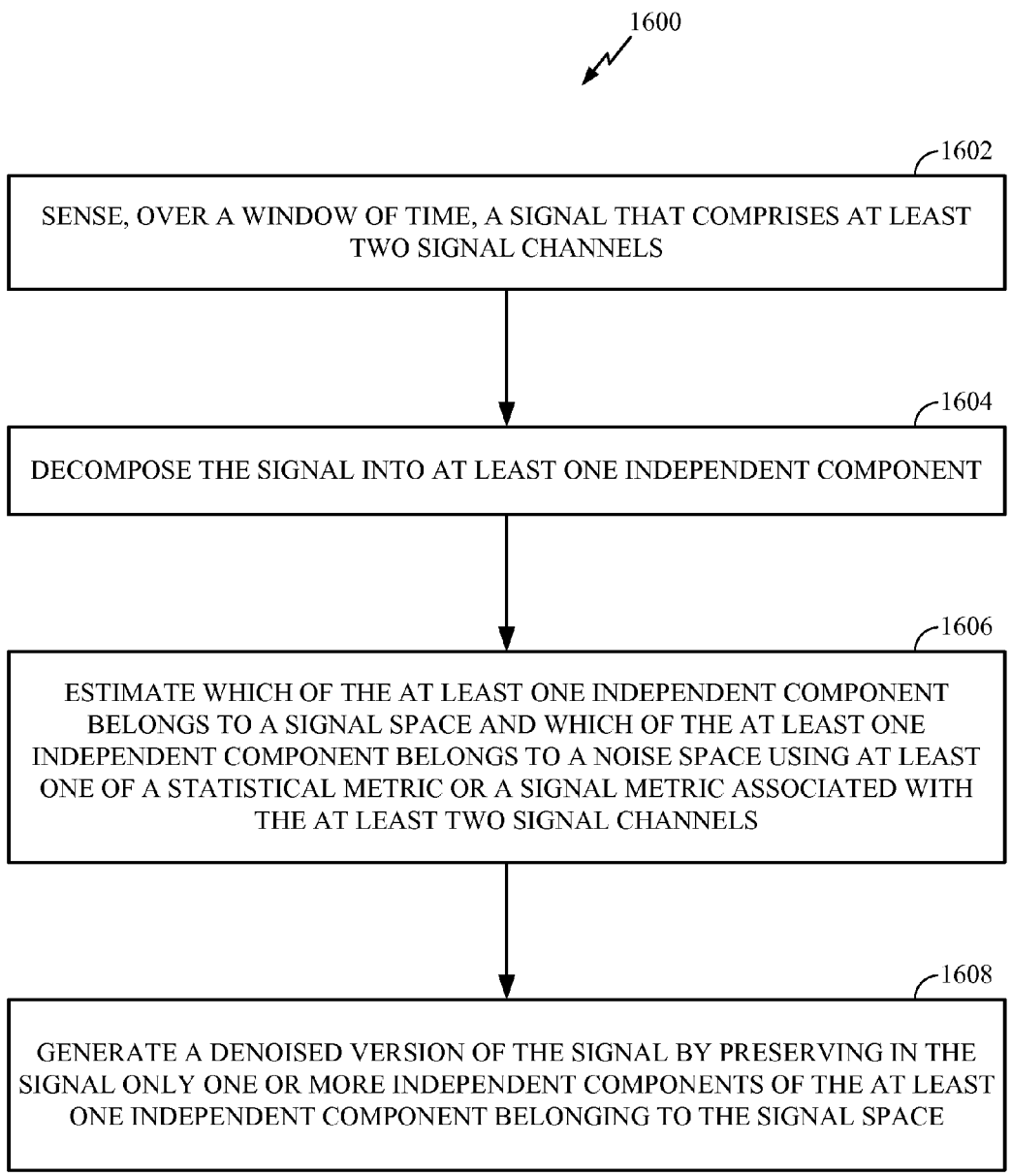
FIG. 16 illustrates example operations that may be performed at a sensor device for denoising physiological signals in accordance with certain aspects of the present disclosure.

FIG. 16 illustrates example operations 1600 that may be performed at a sensor device (e.g., at the acquisition circuits 102, 104, 106, 108 of the BAN 100 from FIG. 1 and/or at the aggregator 110 of the BAN 100) for de-noising physiological signals in accordance with certain aspects of the present disclosure. At 1602, a signal that comprises at least two signal channels may be obtained. At 1604, the signal may be decomposed into at least two independent components. At 1606, the sensor device may estimate which of the at least two independent components belong to a signal space and which of the at least two independent components belong to a noise space using a statistical metric associated with the at least two signal channels. At 1608, de-noised version of the signal may be generated by preserving in the signal only one or more independent components of the at least two independent components belonging to the signal space. According to certain aspects of the present disclosure, the signal may comprise an ECG signal.

In an aspect of the present disclosure, the sensor device may perform refining estimation of which of the independent components belong to the signal space using an updated threshold associated with the statistical metric, the threshold being updated based on the de-noised version of signal. In an aspect, updating the threshold may comprise: performing feature extraction on the de-noised version of signal to obtain one or more features of the de-noised version of signal, performing temporal clustering of the de-noised version of signal using the one or more features, determining, based on the temporal clustering, drifts of centroids associated with the signal channels relative to values of the centroids, and updating the threshold based on the determined drifts.

Figure 16A:
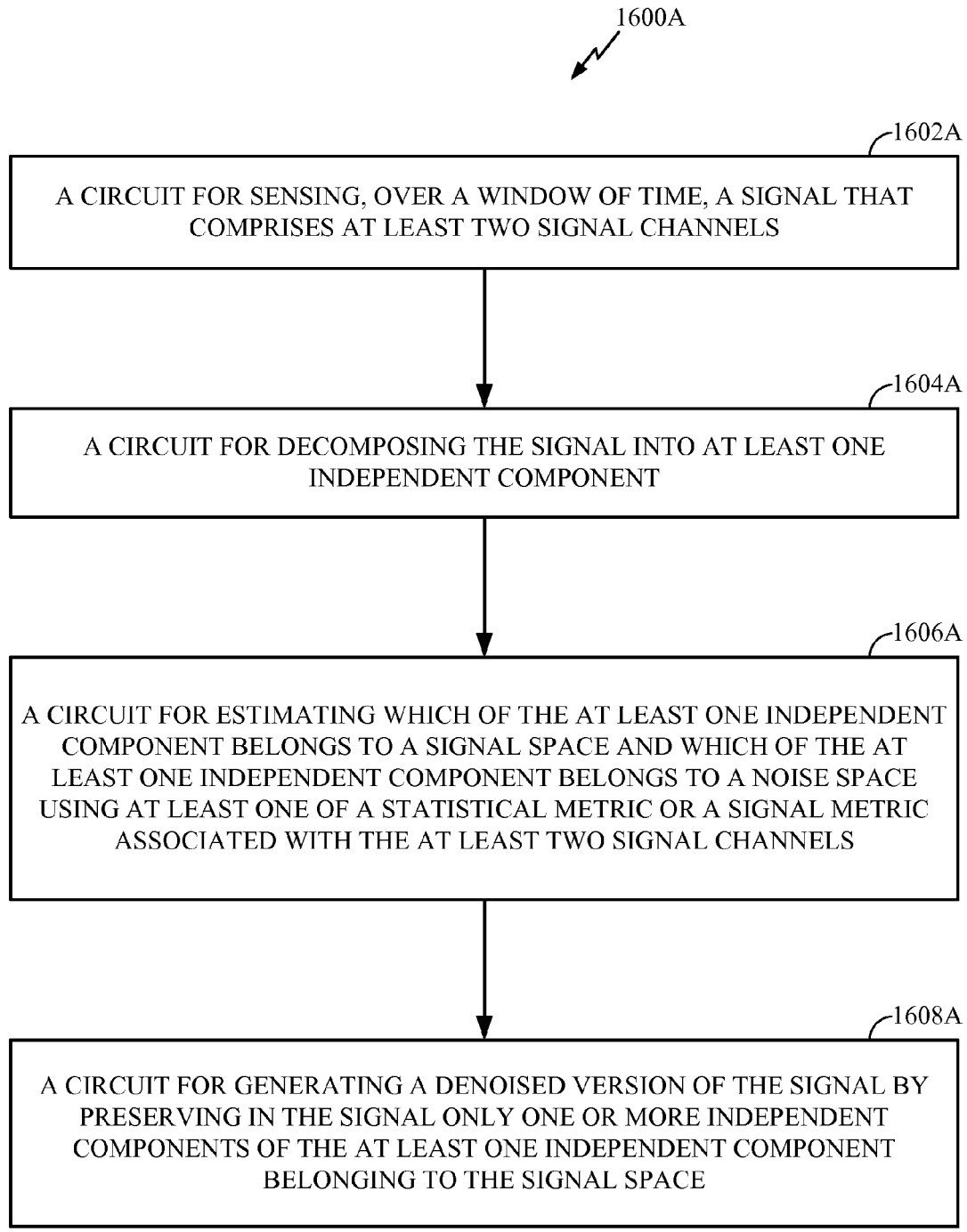
FIG. 16A illustrates example operations that may be performed at a sensor device for denoising physiological signals using example components in accordance with certain aspects of the present disclosure.

FIG. 16A illustrates example operations 1600A that may be performed at a sensor device (e.g., at the acquisition circuits 102, 104, 106, 108 of the BAN 100 from FIG. 1, at the aggregator 110 of the BAN 100, at the wireless device 202 from FIG. 2, and/or at the sensor device 500 from FIG. 5) for de-noising physiological signals using example components in accordance with certain aspects of the present disclosure. At 1602A, a circuit of the sensor device (e.g., a PPG sensor, an ECG sensor, an EEG sensor, a 3D-Accl sensor, or a circuit of the aggregator 110) may be configured to obtain a signal that comprises at least two signal channels. At 1604A, an independent component analysis (ICA) module of the sensor device (e.g., the signal detector 218 from FIG. 2 and/or the ICA processing unit 512 from FIG. 5) may be configured to decompose the signal into at least two independent components. At 1606A, an independent component (IC) denoising module of the sensor device (e.g., the signal detector 218 from FIG. 2 and/or the IC denoising module 502 from FIG. 5) may be configured to estimate which of the at least two independent components belong to a signal space and which of the at least two independent components belong to a noise space using a statistical metric associated with the at least two signal channels. At 1608A, circuitry of the sensor device (e.g., the signal detector 218, the processor 204 and/or the DSP 220 from FIG. 2, and/or at least one of the modules 502, 504, 506 from FIG. 5) may be configured to generate a de-noised version of the signal by preserving in the signal only one or more independent components of the at least two independent components belonging to the signal space.

In an aspect of the present disclosure, the circuit of the sensor device configured to obtain the signal may comprise a sensor (e.g., a PPG sensor, an ECG sensor, an EEG sensor, a 3D-Accl sensor, etc) configured to sense the signal over a window of time. In an aspect, the statistical metric may comprise a ratio of a first metric and a second metric for each of the independent components. The first metric may be based on a kurtosis of the independent component of the signal in the window, and the second metric may be based on a variance of means of samples of the independent component in sub-windows within the window. Further, the independent component may belong to the noise space if the ratio is below a threshold. In an aspect of the present disclosure, a feature extraction module of the sensor device (e.g., the feature extraction module 504 from FIG. 5) may be configured to determine a centroid for each of the signal channels based on a feature vector derived from the de-noised version of signal.

In an aspect, circuitry of the sensor device (e.g., the processor 204 from FIG. 2, the feature extraction module 504 from FIG. 5, and/or the temporal clustering module 506 from FIG. 5) may be configured to update a threshold associated with the statistical metric based on the de-noised version of signal. Further, the IC denoising module (e.g., the signal detector 218 and/or the module 502) may be also configured to refine estimation of which of the independent components belong to the signal space using the updated threshold.

According to certain aspects, circuitry of the sensor device (e.g., the processor 204 and/or the modules 504, 506) may be also configured to perform feature extraction on the de-noised version of signal to obtain one or more features of the de-noised version of signal, perform temporal clustering of the de-noised version of signal using the one or more features, determine, based on the temporal clustering, drifts of centroids associated with the signal channels relative to values of the centroids, and update the threshold based on the determined drifts. The feature extraction may comprise extraction of spectral features of the de-noised version of signal. Alternatively or additionally, the feature extraction may comprise extraction of morphological features of the de-noised version of signal.

According to certain aspects, circuitry of the sensor device (e.g., the processor 204 and/or the modules 504, 506) may be further configured to update a threshold associated with the statistical metric based on the de-noised version of signal, wherein the IC denoising module (e.g., the signal detector 218 and/or the module 502) may be also configured to refine further estimation of which of the independent components of a later portion of the signal belong to the signal space using the updated threshold. The statistical metric may comprise a ratio of a first metric and a second metric for each of the independent components, and the independent component may belong to the noise space if the ratio is below the updated threshold.

In an aspect of the present disclosure, circuitry of the sensor device (e.g., the processor 204 and/or the modules 504, 506) may be configured to reconstruct a version of the signal using the independent components belonging to the signal space. For example, the circuitry may comprise a feature extraction module (e.g., the module 504) configure to obtain a feature vector of the signal based on the de-noised version of the signal, and a temporal clustering module (e.g., the module 506) configured to perform temporal clustering of the de-noised version of the signal using the feature vector.

The various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in Figures, those operations may have corresponding counterpart means-plus-function components with similar numbering. For example, operations 1600 illustrated in FIG. 16 correspond to components 1600A illustrated in FIG. 16A.

For example, the means for obtaining may comprise an application specific integrated circuit, e.g., the signal detector 218 of the wireless device 202 from FIG. 2, and/or the processor 204 of the wireless device 202. The means for decomposing may comprise an application specific integrated circuit, e.g., the processor 204 and/or the signal detector 218. The means for estimating may comprise an application specific integrated circuit, e.g., the processor 204 and/or the signal detector 218. The means for generating may comprise an application specific integrated circuit, e.g., the processor 204 and/or the signal detector 218. The means for sensing may comprise an application specific integrated circuit, e.g., the signal detector 218. The means for determining may comprise an application specific integrated circuit, e.g., the processor 204 and/or the signal detector 218. The means for updating may comprise an application specific integrated circuit, e.g., the processor 204. The means for utilizing may comprise an application specific integrated circuit, e.g., the processor 204. The means for refining estimation of signal components may comprise an application specific integrated circuit, e.g., the processor 204 and/or the signal detector 218. The means for refining further estimation of signal components may comprise an application specific integrated circuit, e.g., the processor 204 and/or the signal detector 218. The means for performing feature extraction may comprise an application specific integrated circuit, e.g., the processor 204 and/or the signal detector 218. The means for performing temporal clustering of a signal may comprise an application specific integrated circuit, e.g., the processor 204 and/or the signal detector 218. The means for reconstructing may comprise an application specific integrated circuit, e.g., the processor 204 and/or the signal detector 218.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logical blocks, modules and circuits described in connection with the present disclosure may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the present disclosure may be embodied directly in hardware, in a software module executed by a processor, or in a combination of the two. A software module may reside in any form of storage medium that is known in the art. Some examples of storage media that may be used include random access memory (RAM), read only memory (ROM), flash memory, EPROM memory, EEPROM memory, registers, a hard disk, a removable disk, a CD-ROM and so forth. A software module may comprise a single instruction, or many instructions, and may be distributed over several different code segments, among different programs, and across multiple storage media. A storage medium may be coupled to a processor such that the processor can read information from, and write information to, the storage medium. In the alternative, the storage medium may be integral to the processor.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

The functions described may be implemented in hardware, software, firmware, or any combination thereof. If implemented in software, the functions may be stored or transmitted over as one or more instructions or code on a computer-readable medium. Computer-readable media include both computer storage media and communication media including any medium that facilitates transfer of a computer program from one place to another. A storage medium may be any available medium that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared (IR), radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk, and Bluray® disc where disks usually reproduce data magnetically, while discs reproduce data optically with lasers. Thus, in some aspects computer-readable media may comprise non-transitory computer-readable media (e.g., tangible media). In addition, for other aspects computer-readable media may comprise transitory computer-readable media (e.g., a signal). Combinations of the above should also be included within the scope of computer-readable media.

Thus, certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

A wireless device (a wireless node) in the present disclosure may include various components that perform functions based on signals that are transmitted by or received at the wireless device. A wireless device may also refer to a wearable wireless device. In some aspects the wearable wireless device may comprise a wireless headset or a wireless watch. For example, a wireless headset may include a transducer adapted to provide audio output based on data received via a receiver. A wireless watch may include a user interface adapted to provide an indication based on data received via a receiver. A wireless sensing device may include a sensor adapted to provide data to be transmitted via a transmitter.

A wireless device may communicate via one or more wireless communication links that are based on or otherwise support any suitable wireless communication technology. For example, in some aspects a wireless device may associate with a network. In some aspects, the network may comprise a personal area network (e.g., supporting a wireless coverage area on the order of 30 meters) or a body area network (e.g., supporting a wireless coverage area on the order of 10 meters) implemented using ultra-wideband technology or some other suitable technology. In some aspects, the network may comprise a local area network or a wide area network. A wireless device may support or otherwise use one or more of a variety of wireless communication technologies, protocols, or standards such as, for example, CDMA, TDMA, OFDM, OFDMA, WiMAX, and Wi-Fi. Similarly, a wireless device may support or otherwise use one or more of a variety of corresponding modulation or multiplexing schemes. A wireless device may thus include appropriate components (e.g., air interfaces) to establish and communicate via one or more wireless communication links using the above or other wireless communication technologies. For example, a device may comprise a wireless transceiver with associated transmitter and receiver components (e.g., transmitter 210 and receiver 212) that may include various components (e.g., signal generators and signal processors) that facilitate communication over a wireless medium.

The teachings herein may be incorporated into (e.g., implemented within or performed by) a variety of apparatuses (e.g., devices). For example, one or more aspects taught herein may be incorporated into a phone (e.g., a cellular phone), a personal data assistant ("PDA") or so-called smart-phone, an entertainment device (e.g., a portable media device, including music and video players), a headset (e.g., headphones, an earpiece, etc.), a microphone, a medical sensing device (e.g., a biometric sensor, a heart rate monitor, a pedometer, an EKG device, a smart bandage, etc.), a user I/O device (e.g., a watch, a remote control, a light switch, a keyboard, a mouse, etc.), an environment sensing device (e.g., a tire pressure monitor), a monitoring device that may receive data from the medical or environment sensing device (e.g., a desktop, a mobile computer, etc.), a point-of-care device, a hearing aid, a set-top box, or any other suitable device. The monitoring device may also have access to data from different sensing devices via connection with a network.

These devices may have different power and data requirements. In some aspects, the teachings herein may be adapted for use in low power applications (e.g., through the use of an impulse-based signaling scheme and low duty cycle modes) and may support a variety of data rates including relatively high data rates (e.g., through the use of high-bandwidth pulses).

In some aspects a wireless device may comprise an access device (e.g., an access point) for a communication system. Such an access device may provide, for example, connectivity to another network (e.g., a wide area network such as the Internet or a cellular network) via a wired or wireless communication link. Accordingly, the access device may enable another device (e.g., a wireless station) to access the other network or some other functionality. In addition, it should be appreciated that one or both of the devices may be portable or, in some cases, relatively non-portable. Also, it should be appreciated that a wireless device also may be capable of transmitting and/or receiving information in a non-wireless manner (e.g., via a wired connection) via an appropriate communication interface.

While the foregoing is directed to aspects of the present disclosure, other and further aspects of the disclosure may be devised without departing from the basic scope thereof, and the scope thereof is determined by the claims that follow.

The invention claimed is:

1. An apparatus for signal processing, comprising:
   a circuit configured to obtain a signal that comprises at least two signal channels;
   an independent component analysis (ICA) module configured to decompose the signal into at least two independent components;
   an independent component (IC) denoising module configured to estimate which of the at least two independent components belong to a signal space and which of the at least two independent components belong to a noise space using a statistical metric associated with the at least two signal channels, wherein
   the IC denoising module is also configured to generate a de-noised version of the signal by preserving in the signal only one or more independent components of the at least two independent components belonging to the signal space; and
   circuitry configured to reconstruct a version of the signal using the one or more independent components belonging to the signal space.

2. The apparatus of claim 1, wherein the signal comprises an electrocardiogram (ECG) signal.

3. The apparatus of claim 1, wherein the circuit configured to obtain the signal comprises a sensor configured to sense the signal over a window of time.

4. The apparatus of claim 3, wherein:
   the statistical metric comprises a ratio of a first metric and a second metric for each of the independent components, the first metric is based on a kurtosis of the independent component of the signal in the window, and
   the second metric is based on a variance of means of samples of the independent component in sub-windows within the window.

5. The apparatus of claim 4, wherein the independent component belongs to the noise space if the ratio is below a threshold.

6. The apparatus of claim 1, further comprising:
   a feature extraction module configured to determine a centroid for each of the signal channels based on a feature vector derived from the de-noised version of signal.

7. The apparatus of claim 1, further comprising:
   circuitry configured to update a threshold associated with the statistical metric based on the de-noised version of signal, wherein
   the IC denoising module is also configured to utilize the threshold to estimate which of the independent components belong to the signal space and which of the independent components belong to the noise space.

8. The apparatus of claim 7, wherein the IC denoising module is also configured to:
   refine estimation of which of the independent components belong to the signal space using the updated threshold.

9. The apparatus of claim 7, wherein the threshold updating circuitry is also configured to:
   perform feature extraction on the de-noised version of signal to obtain one or more features of the de-noised version of signal;
   perform temporal clustering of the de-noised version of signal using the one or more features;
   determine, based on the temporal clustering, drifts of centroids associated with the signal channels relative to values of the centroids; and
   update the threshold based on the determined drifts.

10. The apparatus of claim 9, wherein the feature extraction comprises extraction of spectral features of the de-noised version of signal.

11. The apparatus of claim 9, wherein the feature extraction comprises extraction of morphological features of the de-noised version of signal.

12. The apparatus of claim 1, further comprising:
   threshold updating circuitry configured to update a threshold associated with the statistical metric based on the de-noised version of signal, wherein
   the IC denoising module is also configured to refine further estimation of which of the independent components of a later portion of the signal belong to the signal space using the updated threshold, and
   the statistical metric comprises a ratio of a first metric and a second metric for each of the independent components, and the independent component belongs to the noise space if the ratio is below the updated threshold.

13. The apparatus of claim 1, wherein the circuitry comprises:
   a feature extraction module configured to obtain a feature vector of the signal based on the de-noised version of the signal; and
   a temporal clustering module configured to perform temporal clustering of the de-noised version of the signal using the feature vector.

14. A method for signal processing, comprising:
   obtaining a signal that comprises at least two signal channels;
   decomposing the signal into at least two independent components;

estimating which of the at least two independent components belong to a signal space and which of the at least two independent components belong to a noise space using a statistical metric associated with the at least two signal channels;
generating a de-noised version of the signal by preserving in the signal only one or more independent components of the at least two independent components belonging to the signal space; and
reconstructing a version of the signal using the one or more independent components belonging to the signal space.

15. The method of claim 14, wherein the signal comprises an electrocardiogram (ECG) signal.

16. The method of claim 14, wherein obtaining the signal comprises sensing the signal over a window of time.

17. The method of claim 16, wherein:
the statistical metric comprises a ratio of a first metric and a second metric for each of the independent components,
the first metric is based on a kurtosis of the independent component of the signal in the window, and
the second metric is based on a variance of means of samples of the independent component in sub-windows within the window.

18. The method of claim 17, wherein the independent component belongs to the noise space if the ratio is below a threshold.

19. The method of claim 14, further comprising:
determining a centroid for each of the signal channels based on a feature vector derived from the de-noised version of signal.

20. The method of claim 14, further comprising:
updating a threshold associated with the statistical metric based on the de-noised version of signal; and
utilizing the threshold to estimate which of the independent components belong to the signal space and which of the independent components belong to the noise space.

21. The method of claim 20, further comprising:
refining estimation of which of the independent components belong to the signal space using the updated threshold.

22. The method of claim 20, wherein updating the threshold comprises:
performing feature extraction on the de-noised version of signal to obtain one or more features of the de-noised version of signal;
performing temporal clustering of the de-noised version of signal using the one or more features;
determining, based on the temporal clustering, drifts of centroids associated with the signal channels relative to values of the centroids; and
updating the threshold based on the determined drifts.

23. The method of claim 22, wherein the feature extraction comprises extraction of spectral features of the de-noised version of signal.

24. The method of claim 22, wherein the feature extraction comprises extraction of morphological features of the de-noised version of signal.

25. The method of claim 14, further comprising:
updating a threshold associated with the statistical metric based on the de-noised version of signal; and
refining further estimation of which of the independent components of a later portion of the signal belong to the signal space using the updated threshold, wherein
the statistical metric comprises a ratio of a first metric and a second metric for each of the independent components, and the independent component belongs to the noise space if the ratio is below the updated threshold.

26. The method of claim 14, wherein the reconstructing comprises:
obtaining a feature vector of the signal based on the de-noised version of the signal; and
performing temporal clustering of the de-noised version of the signal using the feature vector.

27. An apparatus for signal processing, comprising:
means for obtaining a signal that comprises at least two signal channels;
means for decomposing the signal into at least two independent components;
means for estimating which of the at least two independent components belong to a signal space and which of the at least two independent components belong to a noise space using a statistical metric associated with the at least two signal channels;
means for generating a de-noised version of the signal by preserving in the signal only one or more independent components of the at least two independent components belonging to the signal space; and
means for reconstructing a version of the signal using the one or more independent components belonging to the signal space.

28. The apparatus of claim 27, wherein:
the statistical metric comprises a ratio of a first metric and a second metric for each of the independent components,
the first metric is based on a kurtosis of the independent component of the signal in the window, and
the second metric is based on a variance of means of samples of the independent component in sub-windows within the window.

29. The apparatus of claim 28, wherein the independent component belongs to the noise space if the ratio is below a threshold.

30. The apparatus of claim 27, further comprising:
means for determining a centroid for each of the signal channels based on a feature vector derived from the de-noised version of signal.

31. The apparatus of claim 27, further comprising:
means for updating a threshold associated with the statistical metric based on the de-noised version of signal; and
means for utilizing the threshold to estimate which of the independent components belong to the signal space and which of the independent components belong to the noise space.

32. The apparatus of claim 31, further comprising:
means for refining estimation of which of the independent components belong to the signal space using the updated threshold.

33. The apparatus of claim 31, further comprising:
means for performing feature extraction on the de-noised version of signal to obtain one or more features of the de-noised version of signal;
means for performing temporal clustering of the de-noised version of signal using the one or more features;
means for determining, based on the temporal clustering, drifts of centroids associated with the signal channels relative to values of the centroids; and
means for updating the threshold based on the determined drifts.

34. The apparatus of claim 33, wherein the feature extraction comprises extraction of spectral features of the de-noised version of signal.

35. The apparatus of claim 33, wherein the feature extraction comprises extraction of morphological features of the de-noised version of signal.

36. The apparatus of claim 27, further comprising:

means for updating a threshold associated with the statistical metric based on the de-noised version of signal; and means for refining further estimation of which of the independent components of a later portion of the signal belong to the signal space using the updated threshold, wherein the statistical metric comprises a ratio of a first metric and a second metric for each of the independent components, and the independent component belongs to the noise space if the ratio is below the updated threshold.

37. The apparatus of claim 27, further comprising:

means for obtaining a feature vector of the signal based on the de-noised version of the signal; and means for performing temporal clustering of the de-noised version of the signal using the feature vector.

38. A computer program product for signal processing, comprising:

a non-transitory computer-readable medium encoded with instructions executable by a processor to:

obtain a signal that comprises at least two signal channels;

decompose the signal into at least two independent components;

estimate which of the at least two independent components belong to a signal space and which of the at least two independent components belong to a noise space using a statistical metric associated with the at least two signal channels;

generate a de-noised version of the signal by preserving in the signal only one or more independent components of the at least two independent components belonging to the signal space; and reconstruct a version of the signal using the one or more independent components belonging to the signal space.

* * * * *